United States Patent
Tully et al.

(10) Patent No.: US 9,707,703 B2
(45) Date of Patent: Jul. 18, 2017

(54) APPARATUS, KITS AND METHODS FOR THE PRODUCTION OF BIOMIMETIC CONSTRUCTS

(75) Inventors: Francis Michael Neves Zuzarte Tully, Royston (GB); Stephen Owen, Royston (GB); Michael Headlam Purser, Royston (GB); Robert Brown, Stanmore (GB); Tijna Alekseeva, Stanmore (GB)

(73) Assignee: UCL BUSINESS PLC, London (GB)

( * ) Notice: Subject to any disclaimer, the term of this patent is extended or adjusted under 35 U.S.C. 154(b) by 576 days.

(21) Appl. No.: 13/703,336

(22) PCT Filed: Jun. 2, 2011

(86) PCT No.: PCT/GB2011/000844
§ 371 (c)(1),
(2), (4) Date: Dec. 10, 2012

(87) PCT Pub. No.: WO2011/154686
PCT Pub. Date: Dec. 15, 2011

(65) Prior Publication Data
US 2013/0099407 A1  Apr. 25, 2013

Related U.S. Application Data

(60) Provisional application No. 61/353,355, filed on Jun. 10, 2010.

(51) Int. Cl.
*B29B 11/12* (2006.01)
*A61L 27/24* (2006.01)
(Continued)

(52) U.S. Cl.
CPC .............. *B29B 11/12* (2013.01); *A61L 27/24* (2013.01); *A61L 27/3891* (2013.01);
(Continued)

(58) Field of Classification Search
CPC ...... B29B 11/12; A61L 27/24; A61L 27/3891; A61L 27/52; A61L 27/00; C12M 21/08;
(Continued)

(56) References Cited

U.S. PATENT DOCUMENTS

| 2008/0131473 A1 | 6/2008 | Brown et al. |
| 2011/0091922 A1 | 4/2011 | Krishnan et al. |
| 2011/0104798 A1 | 5/2011 | Tschumperlin et al. |

FOREIGN PATENT DOCUMENTS

| WO | WO 2006/003442 A2 | 1/2006 |
| WO | WO 2009/032164 A1 | 3/2009 |

OTHER PUBLICATIONS

Patent Cooperation Treaty International Search Report dated Oct. 11, 2011 from International Application No. PCT/GB2011/000844 titled Apparatus, Kits and Methods for the Production of Biomimetic Constructs.

(Continued)

*Primary Examiner* — Matthew Daniels
*Assistant Examiner* — Leith S Shafi
(74) *Attorney, Agent, or Firm* — Hamilton, Brook, Smith & Reynolds, P.C.

(57) ABSTRACT

This invention relates to apparatus, kits and methods for the production of biomimetic constructs by plastically compressing a gel, such as a collagen gel, in a well using a plunger, which may be porous. The apparatus, kits and methods allow biomimetic constructs to be produced in a controlled and reproducible manner and are suitable for the production of multilayered constructs.

10 Claims, 18 Drawing Sheets

(51) Int. Cl.
    *A61L 27/38*     (2006.01)
    *A61L 27/52*     (2006.01)
    *C12M 3/00*     (2006.01)
    *C12M 1/32*     (2006.01)
    *C12M 1/12*     (2006.01)
    *C12N 5/00*     (2006.01)

(52) U.S. Cl.
    CPC .............. *A61L 27/52* (2013.01); *C12M 21/08* (2013.01); *C12M 23/12* (2013.01); *C12M 25/14* (2013.01); *C12N 5/0068* (2013.01); *C12N 2533/54* (2013.01)

(58) Field of Classification Search
    CPC ... C12M 23/12; C12M 25/14; C12N 2533/54; C12N 5/0068
    USPC .............. 425/84; 435/29, 288.7, 325, 305.2; 506/33; 427/331; 264/86, 334, 337
    See application file for complete search history.

(56) References Cited

OTHER PUBLICATIONS

Patent Cooperation Treaty International Preliminary Report on Patentability dated Dec. 10, 2012 from International Application No. PCT/GB2011/000844 titled Apparatus, Kits and Methods for the Production of Biomimetic Constructs.

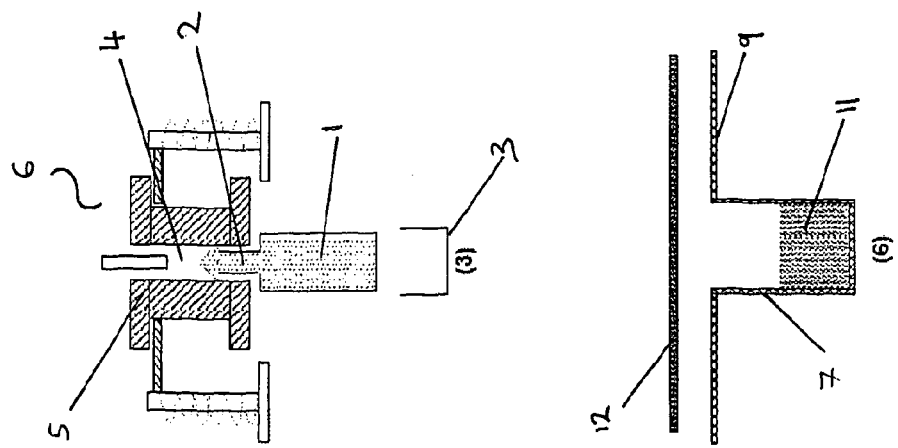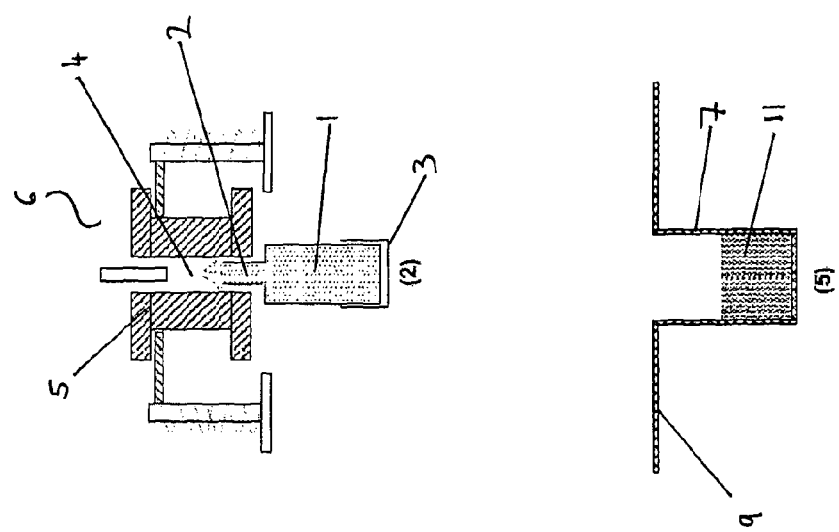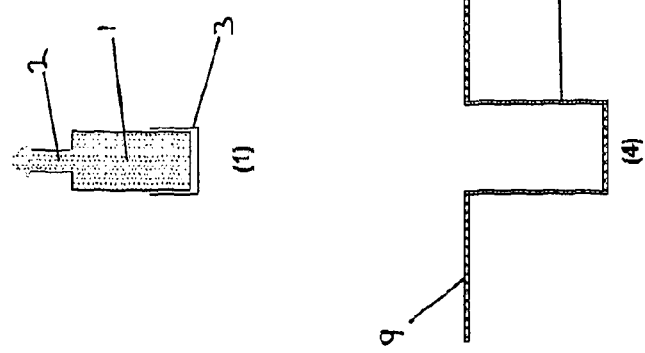
Figure 2a

APPARATUS, KITS AND METHODS FOR THE PRODUCTION OF BIOMIMETIC CONSTRUCTS

This application is the U.S. National Stage of International Application No. PCT/GB2011/000844, filed Jun. 2, 2011, which designates the U.S., published in English, and claims the benefit of U.S. Provisional Application No. 61/353,355, filed Jun. 10, 2010.

This invention relates to apparatus, kits and methods for producing biomimetic constructs.

Conventionally, tissue-engineering aims to convert an initial cell-scaffold construct into a tissue-like architecture which has biomimetic function. This conversion process generally involves cell-based remodelling in culture. However, in most cases, cell-based remodelling has proved slow (often taking weeks), difficult to control and costly with only limited ability to organise bioartificial materials or 'tissues' (M. Eastwood et al, *Cel. Motil. Cytoskel.* 1998 40 13; D. Huang, et al *Ann, Biomed. Eng.* 1993 21 289). This is partly attributable to limitations of perfusion/hypoxia which are related to tissue density (e.g. in ligament, dermis and muscle). It is compounded by a limited understanding of how cells actually produce particular native micro-structures (i.e. 3D cell-matrix organisation). The material composition and, more particularly, the 3D nano-micro (meso) scale structure of bioartificial, engineered constructs are critical to their success (R. A. Brown, in *Future Strategies for Tissue and Organ Replacement* (Eds: J. M. Polak, L. L. Ranch, P. Kemp), World Scientific Publishing, Singapore (2002) 48; R. A. Brown at al *Wound Rep. Reg.* (1997) 5 212).

Compressed collagen gels have been used to produce tissue equivalent implants. However, known compression methods are not reproducible or susceptible to automation. Processes and apparatus for the precise and reproducible production of compressed collagen gels are essential to the production of artificial tissue for therapeutic and modelling purposes.

This invention relates to the development of processes and apparatus for the controlled reproducible production of biomimetic constructs.

These biomimetic constructs may be useful as artificial tissue, for example, in therapeutic methods as well vitro modelling and screening methods.

An aspect of the invention provides a method of producing a biomimetic construct comprising:
 (i) introducing a gel solution to a well,
 (ii) incubating the gel solution to form a gel,
 (iii) introducing a plunger to the well,
 (iv) compressing the gel with the plunger such that liquid is expelled from the gel, and
 (v) removing the plunger to leave said biomimetic construct in the well.

A gel may comprise one or more gel-forming polymers. Suitable gel-forming polymers include natural gel-forming polymers, for example proteins such as collagen, laminin, silk, fibrin or elastin, glycoproteins such as fibronectin, and polysaccharides such as chitin, or cellulose, and synthetic gel-forming polymers, for example organic polymers, such as polylactone, polyglycone, polycapryolactone and synthetic polypeptides, and inorganic polymers such as phosphate glass.

In some embodiment, a gel may comprise two, three or more gel-forming polymers. For example, a gel may comprise collagen and one or more non-collagen gel-forming polymers as set out above.

In preferred embodiments, the gel is a collagen gel. A method of producing a biomimetic construct may comprise:
 (i) introducing a collagen solution to a well,
 (ii) incubating the collagen solution to form a collagen gel,
 (iii) introducing a plunger to the well,
 (iv) compressing the gel with the plunger such that liquid is expelled from the gel, and
 (v) removing the plunger to leave said biomimetic construct in the well.

Collagen is a hydrogel comprising fibrils of collagen in an interstitial liquid. Collagen gels are generally isotropic and the collagen fibres are randomly orientated. Native fibril forming collagen types may be preferred in collagen gels including collagen types are I, II, III, V, VI, IX and XI and combinations of these (e.g. III, V or II, IX, XI). Preferably, native type I collagen is employed.

A collagen gel may comprise collagen and one more non-collagen gel-forming polymers include natural and synthetic gel-forming polymers, as described above.

The initial volume of the gel solution (e.g. a collagen solution or non-collagen gel solution) used to produce a layer of compacted gel construct will depend on the production methods and the design and intended use of the compressed construct. For example, a gel solution may have a volume of 0.1 to 10 ml, for example 1, 2, 3, 4, or 5 ml. In some preferred embodiments, 2 to 3.5 ml of gel solution may be used to produce a compressed construct of about 100-150 um thickness. The amount of gel solution employed depends on the height and cross-sectional area of the gel to be produced. For example, to produce a gel with a height of 3 mm to 10 mm in a 6 mm diameter well (28 $mm^2$) 0.08 ml to 0.28 ml of gel solution may be employed. To produce a gel with a height of 3 mm to 16 mm in a 110 mm×75 mm well, 24 ml to 132 ml of gel solution may be employed.

In some embodiments, the collagen solution or non-collagen gel solution may be seeded with cells before is allowed to solidify into a gel. Seeding may occur either before or after introduction to the well. Seeding of the gel, solution is preferably performed under suitable conditions of temperature, pH, ionic strength and sheer to maintain viability, prior to gel formation.

Suitable cells include eukaryotic cells in particular higher eukaryotic cells, such as plant cells and animal cells.

In some embodiments, the cells may be mammalian cells, for example, cells that confer tissue functionality and provide structures which replace or facilitate the repair of endogenous tissue. For example, the gel may comprise one or more of muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, stem cells, such as bone marrow-derived or embryonic stem cells, dermal fibroblasts, skin keratinocytes, (and combination layers of the two), Schwann cells for nerve implants, smooth muscle cells and endothelial cells for vessel structures, urothelial and smooth muscle cells for bladder/urethra structures and osteocytes, chondrocytes, and tendon cells for bone and tendon structures. In some embodiments, the cells seeded into the gel may include fibroblasts such as mouse or human dermal fibroblasts, including neonatal dermal fibroblasts, and human blood vessel fibroblasts Cells may be seeded into the gel solution, which may be a collagen or a non-collagen gel solution, at a density of $1\times10^3$ or $1\times10^4$ to $1\times10^6$ cells/ml, preferably about $1\times10^5$ cells/ml.

Cells may be distributed within the gel in any arrangement. For example, the cells may be distributed homogeneously throughout the gel or distributed in defined zones, regions or layers within the gel.

The gel solution may be introduced into the well by standard liquid handling techniques.

The gel solution, which may be a collagen solution or non-collagen gel solution and may optionally contain cells, may then be solidified into a gel. For example, the solidification of gel solutions, such as collagen solutions, into gels is well-known in the art and typically involves heating for example to 36° C. to 38° C. For example, collagen solution may be induced to polymerise (aggregate) into a gel by incubation at about 37° at neutral pH.

The average density of a seeded gel (e.g. the average collagen density of a seeded collagen gel) before compression may be 0.5 to 5 mg/ml, preferably 1.5 to 4 mg/ml.

In some preferred methods, the plunger is porous. Liquid expelled from the gel during compression is absorbed by the porous plunger. For example, the plunger may comprise a sintered or non-sintered material, such as plastic, cellulose, for example cellulose acetate, plaster, fibre mesh, metals, or ceramics. The plunger is preferably adapted to seal the opening of the well when it is introduced, such that liquid enters the plunger and is not expelled from the well by compression.

In some embodiments, the collagen or non-collagen gel may have a single FLS, which is the surface which contacts the porous plunger i.e. all liquid expulsion from the gel is directed through the gel surface which contacts the porous plunger the FLS.

Following setting, the gel in the well is subjected to plastic compression using the plunger.

Plastic compression of the gel causes it to deform and reduce its volume, such that the gel retains or substantially retains its new volume, even after the compression is removed. Plastic compression is described in more detail in WO2006/03442, Brown R A et al (2005) Adv. Funct. Mat. 15: 176-177, and elsewhere.

The surface of the gel through which liquid is expelled when compression is applied to the gel is generally termed a fluid leaving surface (FLS). The extent of compression may be measured by the amount of liquid expelled through the ELS by plastic compression per unit of surface area of the FLS i.e. $V_{expelled}mm^3/A_{FLS}mm^2$. This is a height reduction which may be expressed in mm. A suitable volume of liquid expelled through the FLS by plastic compression per unit of FLS surface area may be 2 to 16.5 mm, for example 3, 4, 5, 6, 7, 8, 9, 10, 11, 12, 13, 14, 15 or 16 mm, and preferably 2 to 14 mm, 2.5 to 13 or 5 to 10 mm.

Plastic compression may reduce the volume of the gel by 80% to 99.5%. For example, the compressed gel may have 1, 2, 3, 4 or 5% of its original volume. In some preferred embodiments, at east 95%, 96%, 97%, 98% or 99% w/w of the liquid in the gel may be expelled.

In some embodiments, the surface of the compressed gel construct (e.g. compressed collagen or non-collagen construct) may be seeded with cells, after compression.

After compression and optional seeding, a cell-containing gel construct may be incubated in culture medium in the well. Suitable conditions are well known in the art. The length and conditions of incubation will depend on the intended application. Typically, where the surface of a construct has been seeded, the construct may be incubated until a confluent layer forms on the surface, for example 1, 2, 3, 4, 5, 6, 7, 8, 9 or 10 or more days.

In some embodiments, the methods may be repeated to produce a multi-layer construct. For example, a method may further comprise:
(vi) introducing a further gel solution onto the compressed gel layer in the well,
(vii) incubating the further gel solution to form a further gel,
(viii) introducing a porous plunger to the well
(ix) compressing the further gel with the plunger such that liquid is expelled from the gel into the plunger,
(x) removing the plunger to leave a construct comprising multiple layers of compressed gel in the well.

Preferably the gel is collagen. A method may further comprise:
(vi) introducing a further collagen solution onto the compressed collagen layer in the well,
(vii) incubating the further collagen solution to form a further collagen gel,
(viii) introducing a porous plunger to the well
(ix) compressing the further collagen gel with the plunger such that liquid is expelled from the collagen gel into the plunger,
(x) removing the plunger to leave a collagen construct comprising multiple layers of compressed collagen in the well.

The further gel solution, for example the further collagen solution, may be seeded with cells, which may be the same or different cells to the original gel solution.

In some embodiments, the porous plunger may be the same plunger which was used in the first compression step. In other embodiments, a different porous plunger may be used for each compression step, Steps (vi) to (x) may be repeated one or more times to produce a biomimetic construct comprising multiple layers of compressed gel, for example multiple layers of compressed collagen.

Any combination of acellular and cell-seeded layers, for example acellular and cell-seeded collagen layers, may be produced depending on requirements. Different cell-types may be seeded into different layers. For example, two or more of the multiple layers of compressed gel may be seeded with the same or different types of cells.

Repeated cycles of gel introduction and compaction allow the production of biomimetic multiple layered tissues.

In some embodiments, the plunger may comprise one or more projections which emboss recesses, pockets or crypts into the surface of the compressed gel. Suitable projections may be located on the surface of the plunger which contacts the gel, i.e. the bottom surface. These embossed microstructures may be useful as niches to support specific cell-types, such as stem cells. The projections may be integral to the plunger and may be produced from the same material as the plunger or a different material, which may be permeable or impermeable, depending on the application. Alternatively, a separate stamp comprising one or more projections may be inserted between the plunger and the gel to emboss recesses or crypts. The separate stamp may be permeable or impermeable, depending on the application.

In some embodiments, the plunger or the separate stamp may comprise one or more projections which emboss grooves into the surface of the compressed gel.

The one or more grooves may be of any suitable width, depth or length for a desired application. Preferably, the grooves extend from an edge of the compressed gel and more preferably extend between 2 or more edges of the compressed gel. In other embodiments, the grooves may not extend to any edge of the compressed gel.

The grooves may be at least 1, at least 10, at least 20, at least 30, at least 40, or at least 50 μm wide and up to 500, up to 400, up to 300, up to 200 or up to 100 μm wide. The ranges of suitable widths for grooves as described herein may have any of these minimum values in combination with any of these maximum values. For example, suitable grooves may be 1 to 500 μm, preferably 1 to 300 μm wide.

The grooves may be at least 1, at least 5, or at least 10, at least 20, at least 30, at least 40, or at least 50 μm deep and up to 500, up to 400, up to 300, up to 200 or up to 100 μm deep. The ranges of suitable depths for grooves as described herein may have any of these minimum values in combination with any of these maximum values. For example, suitable grooves may be 1 to 500 μm, preferably 1 to 300 μm deep.

The grooves may be up 110 mm, up 80 mm, up 75 mm, up 50 mm, up to 30 mm, up to 20 mm, up to 10 mm, or up to 6 mm long, for example up to 22 mm long. In some preferred embodiments, the grooves may extend across the compressed gel from one edge to another, and so may have a length which corresponds to the width, length or diameter of the compressed gel. In other embodiments, the grooves may not extend to an edge of the compressed gel or may extend to a single edge of the compressed gel.

The grooves may be at least 10, at least 20, or at least 50 μm long. The ranges of suitable length for grooves as described herein may have any of these minimum values in combination with any of these maximum values. For example, suitable grooves may be 10 μm to 110 mm long.

Different grooves on the surface of the compressed gel may have the same or different dimensions.

The depth and/or width of a groove may vary along its length. This may be useful in producing enclosed conduits whose transverse cross-sectional area (i.e. the width and/or height of the conduit) varies, for example, increases or decreases, along its length. For example, the conduit may be narrower and/or shallower in parts of the multi-layered construct and wider and/or deeper in other parts of the multi-layered construct.

The dimensions and arrangement of the grooves is determined by the dimensions and arrangement of the projections on the plunger or stamp. For example, groove depth may be 25% to 100% of the projection depth and the groove width may be 75% to 100% of the projection width, preferably 100%.

In one embodiments, a groove in the surface of the compressed gel may divide or split into multiple separate grooves. Multiple separate grooves in the surface of the compressed gel may merge or join together into a single groove.

The one or more embossed grooves may be covered with a further layer of compressed gel, for example a further layer of compressed collagen, to produce one or more enclosed conduits (i.e. roofed channels or microchannels). For example, a further gel solution, for example a further collagen solution, may be introduced onto the surface of the compressed gel layer with the one or more embossed grooves. The further gel solution on the surface may be incubated to form a further gel and then compressed, for example using a porous plunger as described above, to expel liquid from the further gel into the plunger. The compressed further gel covers the one or more embossed grooves to produce a multi-layered construct which contains one or more enclosed (or roofed) conduits or microchannels. The enclosed (or roofed) conduits or microchannels may comprise at least one opening at a surface of the multi-layered construct.

Further layers of compressed collagen or further layers of compressed non-collagen gel may be added to the compressed further gel as described above to produce a multi-layered compressed gel construct. One, two, three, four or more of the layers of compressed gel in the construct may contain embossed grooves.

For example, a biomimetic construct produced as described herein may comprise roofed channels in 10% or more, 25% or more, 50% or more, 75% or more or 100% of the layers of compressed collagen or non-collagen gel in the construct. In some embodiments, the multi-layered biomimetic construct may comprise one, two, three, or four or more layers that lack roofed channels.

The dimensions, number, geometry and arrangement of the roofed channels may be controlled by altering the dimensions, number, geometry and arrangement of the projections on the plunger or stamp in accordance with the desired properties of the biomimetic construct.

In some embodiments, the plunger or separate stamp may comprise one or more elongated projections which emboss channels which link roofed channels in different layers of a multi-layered biomimetic construct.

The provision of roofed channels may be useful in providing biomimetic constructs which contain micro-channels of controllable dimensions, geometry and direction. The micro-channels may improve the properties of the biomimetic construct, for example, by increasing oxygenation within the biomimetic construct and/or promote the ingrowth of blood vessels and nerve elements after implantation.

Methods of the present invention are particularly suitable for the production of biomimetic constructs in an array of wells simultaneously. This may be useful, for example, in screening.

Suitable kits and apparatus for producing arrays of wells containing biomimetic constructs are described below.

In some embodiments, the bottom of the well may be permeable. For example, liquids such as culture medium may pass into the well through the permeable bottom. Conveniently, the bottom of the well may be defined by a membrane. This may be useful, for example, when the cells on the surface of the construct need to be exposed to air to induce a biomimetic phenotype.

The well may be mounted on an impermeable support, such that said permeable well bottom does not contact the support. The well may be accommodated in a pocket or recess of the support. This allows culture medium in the pocket or recess of the support to contact the construct, whilst leaving the upper surface of the construct exposed to the air.

Preferably, the well is resiliently mounted on the support, such that the permeable well bottom can be driven against the impermeable support before compression to prevent the expulsion of liquid from the gel through the permeable well bottom.

For example, the well may be held in a mounting plate which is resiliently mounted on the support. The mounting plate may hold an array of wells, which may be multiple separate wells or a multiple wells linked together, for example in a multi-well plate. The array of wells held in the mounting plate may be accommodated by a corresponding array of pockets or recesses in the support.

Following compression of a gel, the plunger may be removed to leave the compressed gel in the well. In some embodiments, the plunger may be rotated and or tilted to aid separation from the surface of the compressed gel.

In some embodiments, density gradients may be introduced into the compressed gel. For example, a method of producing a biomimetic construct as described herein may comprise:
(i) introducing a collagen solution or a non-collagen gel solution to a well,
(ii) incubating the collagen or non-collagen gel solution to form gel, wherein the gel has a height or depth which is greater at region than at a second region,
(iii) introducing a plunger to the well,
(iv) compressing the gel with the plunger such that liquid is expelled from the gel and the difference in height or depth the gel at the first and second regions is reduced or eliminated, and
(v) removing the plunger to leave said biomimetic construct in the well,
wherein the biomimetic construct has increased stiffness or density in the first region relative to the second region.

Suitable methods for the introduction of density gradients e described in WO2009/004351.

Another aspect of the invention provides a kit for producing a biomimetic construct comprising:
a plunger, and
a well having an opening,
wherein the plunger comprises a porous material and adapted, upon introduction to the well, to seal or partially seal the opening.

The plunger and the well are adapted such that the opening of the well is sealed or partially sealed when the plunger is introduced. In some embodiments, liquid is not expelled out from the well through compression of a collagen or non-collagen gel in the well by the plunger. The porous body of the plunger allows liquid expelled from the collagen or non-collagen gel to enter the plunger. The porous body may be rigid or non-rigid, for example it may display some flexibility or resilience. The porous body made from a non-sintered or sintered material, such as a plastics material, cellulose, plaster, metal, dense fibre or ceramic.

The plunger may further comprise an impermeable support which holds the porous material.

The plunger may comprise a connector, such as a tag or peg, which is attached to the porous body and which allows releasable attachment to a plunger head. The connector is preferably produced from an impermeable material such as plastics material, such as polystyrene, polycarbonate, or polypropylene, or metal to prevent liquid in the porous part of the plunger from entering the plunger holder.

The plunger may be adapted to compress a gel contained in the well and to absorb liquid expelled from the gel by the compression.

The surface of the plunger which contacts the gel in the well during compression may comprise one or more projections which emboss one or more recesses, pockets or grooves into the surface of a collagen or non-collagen gel in the well. Alternatively, a kit may further comprise a separate stamp which comprises one or more projections or other microstructure on its surface. The stamp may be inserted between the plunger and the gel, such that the surface of the gel is embossed by the stamp with one or more one or more recesses, crypts, pockets or grooves upon compression by the plunger.

The projections may be located on the bottom surface of the plunger or stamp i.e. the surface which faces the bottom of the well when the plunger is introduced into the well, and may be absorbent or non-absorbent.

In some embodiments, the plunger may comprise one or more passages extending from an aperture in the top surface of the plunger towards the bottom surface of the plunger. The passages may extend all or part of the way to the bottom surface. For example, the passages may extend 70%, 80%, 90% or 100% of the distance to the bottom surface of the plunger. In some embodiments, the passages may extend to an aperture in the bottom surface of the plunger. Air or other gases or liquids may access the interface between the plunger and the surface of the compressed gel (i.e. the fluid leaving surface) through the one or more passages when the liquid has been expelled from the gel. At the end of the one or more passages, the fluid may exit directly onto the gel through an aperture in the bottom surface of the plunger or the fluid may enter the bottom portion of the plunger adjacent the end of the passages and move through the plunger to exit at its bottom surface.

Air or other fluids may be forced through the one or more passages to facilitate separation of the plunger and the compressed gel. A kit may comprise a driver, such as a piston, which drives or forces fluids through the one or more passages. The driver may be separate from or integral with the plunger. In some embodiments, air and/or the liquid which is absorbed from the gel may be driven through the passages and delivered to the surface of the compressed gel. For example, following absorption of liquid by the plunger, air may be forced through the one or more passages. This air may be delivered directly to the surface of the compressed gel through an aperture in the bottom surface of the plunger; or the air may drive absorbed liquid at the bottom of the plunger back on to the surface of the compressed gel; or a combination of absorbed liquid followed by air may be delivered to the surface of the compressed gel.

The plunger may comprise one or more other features which facilitate separation from the compressed gel.

For example, the plunger may comprise a one or more slots along its exterior extending from the top to the bottom surface of the plunger, such that, upon introduction to the well, the slots and the well define passages that extend from the top of the plunger to the surface of the compressed gel. These passages allow air to access the plunger/gel interface and facilitate separation.

The plunger may comprise a permeable outer layer of paper or synthetic mesh on its bottom surface. This layer may be loosely or partially attached to the plunger and may facilitate the ingress of air to the plunger/gel interface.

The plunger may be removed from the well by removing or partially removing the plunger from the outer layer and then removing the outer layer from the surface of the compressed gel. The outer layer may be conveniently removed by initially separating the outer layer from the gel at an edge or corner of the compressed gel, followed by removal from the remainder of the gel (e.g. peeling it from the edge or corner).

A kit may comprise multiple plungers. For example, an array of plungers may be provided in a tray. The tray may be disposable and may present the plungers with connectors uppermost to facilitate loading. The array of plungers may be quickly and conveniently loaded from the tray into a corresponding array of plunger holders in a collagen or non-collagen gel compression apparatus for producing biomimetic constructs. Suitable apparatus is described below.

A well may be any vessel, pocket or recess which can accommodate a plunger. The well may be made of any suitable material, for example polystyrene, polycarbonate, glass, polypropylene, metals, or ceramics.

In some embodiments, the well or wells may be impermeable. In other embodiments, the well or wells may be permeable. For example, the well or wells may have a permeable bottom, such as a membrane. Permeable wells may have particular applications, for example in airlifting cells being cultured in the wells.

In some embodiments, multiple wells may be linked together. For example, a kit may comprise an array of linked wells. In some embodiments, the kit may include a multi-well plate.

The kit may comprise a plunger for each well in the array. As described above, an array of plungers may be provided in a tray such that each plunger in the array corresponds to a well in the array of wells.

A kit may further comprise a guide plate. This may be useful in embodiments in which the wells are integral with the support (e.g. in a multi-well plate). The guide plate is positioned on the support during compression and contains apertures which correspond to the wells in the support. For example, the guide plate may contain an array of apertures which correspond to an array of wells in the support. The apertures in the guide plate taper inwards from top to bottom i.e. the internal diameter of the apertures at the upper surface is greater than the internal diameter at the lower surface, and the diameter progressively decreases from the upper to the lower surface. At the lower surface of the guide plate, the apertures preferably have the same or reduced internal diameter relative to the wells in the support. During compression, the plungers enter the apertures of the guide plate at the upper surface, where the diameter of the aperture is greatest. As the plungers move through the apertures, the progressively decreasing diameter of the aperture guides the plungers into the wells which are beneath each aperture.

In other embodiments, the kit may comprise multiple single wells. Preferably, the single wells are tapered so that the internal diameter at the opening of the well is greater than the internal diameter at the bottom of the well. This may guide plungers to the bottom of the well and avoid the need for a separate guide plate.

A well may comprise a flange at opening which allows the well to rest on a mounting plate and prevents it from falling through the mounting plate.

The kit ay further comprise a mounting plate or cassette which is adapted to hold multiple wells, for example an array of wells, which may be either linked or separate. The mounting plate may comprise apertures, each of which can accommodate a well.

Preferably, the mounting plate is adapted for resiliently mounting on an impermeable support, for example using resiliently deformable members. The mounting plate may be adapted such that, when positioned on a support, it can be pressed against the support to drive the bottom of a well held in the mounting plate against the support.

A kit may further comprise an impermeable support which is adapted to support the mounting plate, such that wells, in particular permeable wells, held in the mounting plate do not contact the support.

The impermeable support may comprise pockets or recesses which accommodate wells held in the mounting plate. For example, the support may conveniently be a multi-well plate.

A kit may further comprise a lid for covering wells which are accommodated in the mounting plate or integral to the support.

A kit may further comprise reagents useful in producing biomimetic constructs as described herein. Reagents may include collagen, non-collagen gel forming polymers, buffers, nutrient mixes and culture media.

Plungers, wells and other components of a kit may be supplied in a sterile condition in suitable packaging in accordance with standard laboratory practice.

Other aspects of the invention provide kits for producing a biomimetic construct as described herein comprising 2, 3, 4, 5 or more of components selected from the group consisting of: plungers, optionally presented in a disposable tray, wells, mounting plates, optionally with lids, guide plates, impermeable supports, optionally with lids, and reagents. Suitable components are described above.

A kit may be adapted for use in methods of producing biomimetic constructs as described above and may be used in the gel compression apparatus described below.

Another aspect of the invention provides a gel compression apparatus for producing a biomimetic construct comprising:

a mount for a well for containing a collagen gel, and,
a plunger holder for engaging a plunger,
the plunger holder and the mount being movable relative to each other, such that a plunger engaged by the holder is driven into the well in the mount.

The apparatus may be useful in compressing collagen or non-collagen gels.

A plunger which may be engaged by the plunger holder may comprise a porous body and an impermeable support. The porous body may be rigid or non-rigid and may be capable of absorbing liquid expelled during compression of a gel, as described above. The impermeable support may comprise a connector, such as a tag or peg, which is attached to the porous body and which can be releasably attached to the plunger holder. The connector is preferably produced from an impermeable material such as plastics material, such as polystyrene, polycarbonate, or polypropylene, or metal to prevent liquid in the porous part of the plunger from entering the plunger holder.

A suitable well may be any open vessel which accommodates a plunger such that the opening of the well is sealed when the plunger is introduced.

Plungers and wells are described in more detail above.

The plunger holder may be adapted to releasably hold a plunger. For example, the plunger holder may comprise an aperture which accommodates the connector of a plunger and such that the plunger held by friction in the holder.

The plunger holder may further comprise a release for detaching the plunger. For example, the plunger holder may further comprise a probe which is movable through the aperture and dislodges the connector from the aperture and releases the plunger from the holder.

The plunger holder may be movable towards and away from the mount, such that a plunger engaged by the holder is movable into and out of a well positioned in the mount. In other words, the plunger holder is movable between a first position in which a plunger engaged by the holder is accommodated in a well in the mount and a second position in which the plunger is not accommodated in the well.

In some embodiments, the plunger holder may be movable, e.g. rotatable or pivotable, between a compression position for engaging a plunger held therein with the well in the mount and a loading position for loading and/or unloading plungers releasably held by the plunger holder.

The plunger holder may be adapted to engage an array of plungers or more preferably, the apparatus may comprise an array of plunger holders, each plunger holder engaging one of an array of plungers.

The plunger holder may apply sufficient force to the plunger to compress a collagen or non-collagen gel in a well in the mount. For example, the plunger holder may have sufficient mass to apply a gravitational force which compresses the gel. For example, to compress a collagen or non-collagen gel in a well of 10 mm to 22 mm diameter, the plunger holder may have a mass of 5 to 100 g.

In some embodiments, the apparatus may comprise a driver which applies force to the plunger holder to drive the plunger into a well in the mount. A range of different drivers may be employed. For example, the driver may comprise one or more of: one or more weights which are connectable to the plunger holder; a resilient member, such as spring or elastic band which is engaged or engageable with the plunger holder; a motor, for example an electric motor; a hydraulic system for apply fluidic pressure to the plunger.

The force which the driver applies to the plunger holder may be adjustable. For example, the force applied to the plunger holder by the press may be adjusted by altering the number of weights engaged with the plunger holder or adjusting the tension of the resilient member.

The plunger holder may be associated with a guide which facilitates engagement of a plunger held in the holder with a well accommodated in the mount or integral to the support.

The plunger holder may be contained in a plunger head which is adapted to releasably hold an array of plungers.

The plunger holders may be arranged in the plunger head such that each plunger engaged in a holder in the plunger head can be accommodated by a well which is positioned in the mount. For example, the mount may be adapted to accommodate an array of wells which corresponds to the array of plungers releasably held by the plunger holders in the plunger head.

An array of plungers may be held in a tray or plate before releasable attachment to the plunger heads. The apparatus may comprise a loading station suitable for accommodating a tray or plate of plungers. The loading station may also be suitable for accommodating a waste tray for collection of wet plungers after use.

The plunger head may be movable, e.g. rotatable or pivotable, between a compression position for driving a plunger engaged therein into a well in the mount, an unloading position for unloading used plungers from the plunger holders in the plunger head and optionally a loading position for loading plungers into the plunger holders in the plunger head. For example, the plunger head may be movable to a loading position to releasably attach an array of plungers in the loading station into the plunger holders in the head. The plunger head may then be movable to a compression position in which the attached plungers can engage with wells positioned in the mount. The plunger head may then be movable back to an unloading position to release the used plungers, which now contain liquid expelled from the gel and may be discarded. Optionally, a new set of plungers may be loaded.

In some embodiments, the plunger head may be mounted on a post and may be pivoted around the post between the loading and compression positions.

The plunger head may comprise outer guides, for example resilient legs, which are adapted to drive the mounting plate against the support, when these components are being used. The outer guides may also be useful in present allow the plunger head to be precisely positioned above the mount before compression.

The mount may be adapted to accommodate an array of wells, each well accommodating one of the array of plungers.

The mount may comprise a block containing one or more recesses into which wells or supports as described above can be inserted. The block may be flat or may comprise an array of recesses suitable for accommodating an array of wells. Conveniently, the block may accommodate a multiwell plate, for example a 12 or 24 well plate. A multiwell plate mounted on the block may itself be used as a support to accommodate wells, for example individual wells in a mounting plate as described above. This may be useful, for example, when the wells are permeable. Alternatively, the wells of a multiwell plate mounted on the block may be used directly to contain collagen or non-collagen constructs as described herein.

The mount may further comprise one or more heating elements. This allows the incubation of wells in the mount at a user defined temperature, typically about 37° C. This may be useful in setting the collagen or non-collagen gel before compression and in performing subsequent cell culturing steps in the wells, if required. This allows the constructs to remain in situ in the wells in the mount until all the required steps in production are completed.

The compression station of the apparatus may further comprise a lid to cover the mount and the wells accommodated thereon. The lid may be of any rigid, impermeable material, and is preferably transparent. The lid may be useful in maintaining suitable incubation conditions in the mount.

The apparatus may also comprise a timer. This may be useful in timing the duration of the compression applied to the collagen or non-collagen gel in the well, or the length of incubation and culturing steps.

The apparatus may comprise one or more displays for indicating the duration and amount of force applied to the plunger holder, the temperature of the mount and the duration of incubation and/or culturing.

The apparatus may comprise one or more alarms, for example visual or audible alarms, which indicate when the incubation period for setting the collagen or non-collagen gel or the compression period for compressing the gel have elapsed.

An apparatus as described above may comprise a plunger which is engaged with the plunger holder and a well which is positioned on the mount. In some embodiments, the apparatus may comprise an array of plungers and an array of wells. The apparatus may also comprise a support, mounting plate and other consumables described above.

Suitable plungers and wells are described above and the apparatus may comprise a kit as described above.

In some preferred embodiments, an apparatus may comprise a single station in which the mount remains stationary whilst a biomimetic construct produced in a well positioned on the mount.

Alternatively, the apparatus may comprise multiple stations and the mount containing the well in which the biomimetic construct is produced may be movable between the stations. Each station may perform a different operation on the collagen or non-collagen gel in the well. These production line processes may be preferred for highly automated or mass production applications. Automated devices for the manipulation of reagents in multiwell plates are well known in the art.

The mount may be movable between a first station in the apparatus, a second station and optionally a third, fourth, fifth or more station. For example, the mount may move between a dispensing station for adding reagents, such as collagen solution, non-collagen gel forming polymer solution, cell suspensions, and culture media to a well contained in the mount; an incubation station for incubating the collagen or non-collagen gel in the well at a fixed temperature, for example for setting the collagen or non-collagen gel-forming polymer solution and/or culturing cells; and/or a compression station for compression the collagen or non-collagen gel in the well.

The mount may move in a linear fashion between stations or may undergo repeated cycles around the same set of stations for example, the mount may be movable between stations positioned along a rotary indexing system. The mount may be moved between different stations robotically. The design and control of multi-station systems are well-known in the art.

The apparatus may be useful in a method of producing a biomimetic construct as described above. In some embodiments, the apparatus may be used with a kit as described above in the described methods.

An apparatus may be used in a method of producing a biomimetic construct as described above.

Other aspects of the invention provide the use of a kit and/or an apparatus as described above in a method of producing a biomimetic construct. Suitable methods are also described above.

Other aspects of the invention provide methods of producing biomimetic constructs containing roofed microchannels.

A method of producing biomimetic construct comprising a roofed channel may comprise:
(i) providing a compressed gel with one or more grooves on the surface thereof,
(ii) introducing a further gel-forming polymer solution onto the surface of the compressed gel,
(iii) setting the further gel-forming polymer solution to form a further collagen gel, and;
(iv) compressing the further gel such that liquid is expelled the gel.

In other embodiments, a method of producing a biomimetic construct comprising a roofed channel may comprise:
(i) providing a compressed gel with one or more grooves on the surface thereof,
(ii) providing a further gel; and either;
 (a) compressing the further gel such that liquid is expelled; and
 (b) introducing the compressed further gel onto the surface of the compressed gel, or;
 (c) introducing the further gel onto the surface of the compressed gel, and
 (d) compressing the further gel on the surface of the compressed gel.

The compressed further gel forms a roof which encloses the one or more grooves to produce conduits or microchannels.

The compressed gel and/or the further gel-forming polymer solution may be seeded with cells.

In some embodiments, the compressed gel may be provided by compressing a gel with a solid surface, for example the surface of a plunger or stamp as described above, which comprises one or more projections, such that liquid is expelled from the gel and the projections emboss the one or more grooves into the surface of the gel. The solid surface may be permeable or impermeable. Suitable projections and grooves are described in more detail above.

The gel and the further gel may be compressed by any convenient method. For example, a method described above or in WO2006/003442 or Brown R A et al (2005) Adv. Funct. Mat. 15: 176-177 may be employed.

Steps (i) to (iv) may be repeated one or more times to produce a biomimetic construct comprising multiple layers of compressed gel which contains one or more micro-channels.

In preferred embodiments, the gel and the further gel are collagen gels and the gel-forming polymer solution is a collagen solution.

As described above, methods of the invention may be may be useful in producing a biomimetic construct comprising multiple layers of compressed collagen which contains one or more micro-channels or conduits of controllable dimensions, geometry and direction, for example for regenerative medicine applications. The size of the compressed gel and the biomimetic construct depend on the particular application. In some embodiments, the biomimetic construct may be moulded, rolled, folded or otherwise shaped following compression.

The micro-channels or conduits may, for example, increase the core oxygenation and perfusion of the biomimetic construct and promote the ingrowth of blood vessels and nerve elements after implantation.

A methods, kits and apparatus as described above may also be used to produce non-collagen biomimetic constructs using non-collagen gels. For example, an aspect of the invention provides a method of producing a biomimetic construct comprising:
(i) introducing a non-collagen gel solution to a well,
(ii) incubating the non-collagen gel solution to form a gel,
(iii) introducing a plunger to the well,
(iv) compressing the gel with the plunger such that liquid is expelled from the gel, and
(v) removing the plunger to leave said biomimetic construct in the well.

A gel solution is a solution which comprises a gel-forming polymer. Suitable non-collagen gel-forming polymers are described below. A gel solution may be induced to solidify or set into a gel by altering conditions, e.g. temperature.

A non-collagen gel may comprise one or more biocompatible non-collagen gel forming polymers. Suitable non-collagen gel forming polymers include natural gel-forming polymers, for example proteins such as laminin, silk, fibrin, fibronectin or elastin, glycoproteins such as fibronectin, and polysaccharides such as chitin, or cellulose, or synthetic gel-forming polymers, for example organic polymers, such as polylactone, polyglycone, polycapryolactone or synthetic polypeptides and inorganic polymers such as phosphate glass.

Non-collagen gels may be used in the same way as collagen gels to produce biomimetic constructs and all features and aspects of the methods and constructs described above for collagen gels apply mutatis mutandis to non-collagen gels.

Other aspects the invention provide a method, kit and apparatus substantially as described herein and with reference to the accompanying drawings.

Various further aspects and embodiments of the present invention be apparent to those skilled in the art in view of the present disclosure.

All documents mentioned in this specification are incorporated herein by reference their entirety.

"and/or" where used herein is to be taken as specific disclosure of each of the two specified features or components with or without the other. For example "A and/or B" is to be taken as specific disclosure of each of (i) A, (ii) B and A and B, just as if each is set out individually herein.

Unless context dictates otherwise, the descriptions and definitions of the features set out above are not limited to any particular aspect or embodiment of the invention and apply equally to all aspects and embodiments which are described.

Unless the context dictates otherwise, the term "comprises" means including a specified feature and optionally other features. The term thus encompasses both a) "including but not limited to" and b) "consisting of" or "including and limited to". For example "A product comprising A" is to be taken as specific disclosure of both (i) a product including A and (ii) a product consisting of A only, just as if each is set out individually herein.

Certain aspects and embodiments of the invention will now be illustrated by way of example and with reference to the figures and tables described below.

Figure 8:
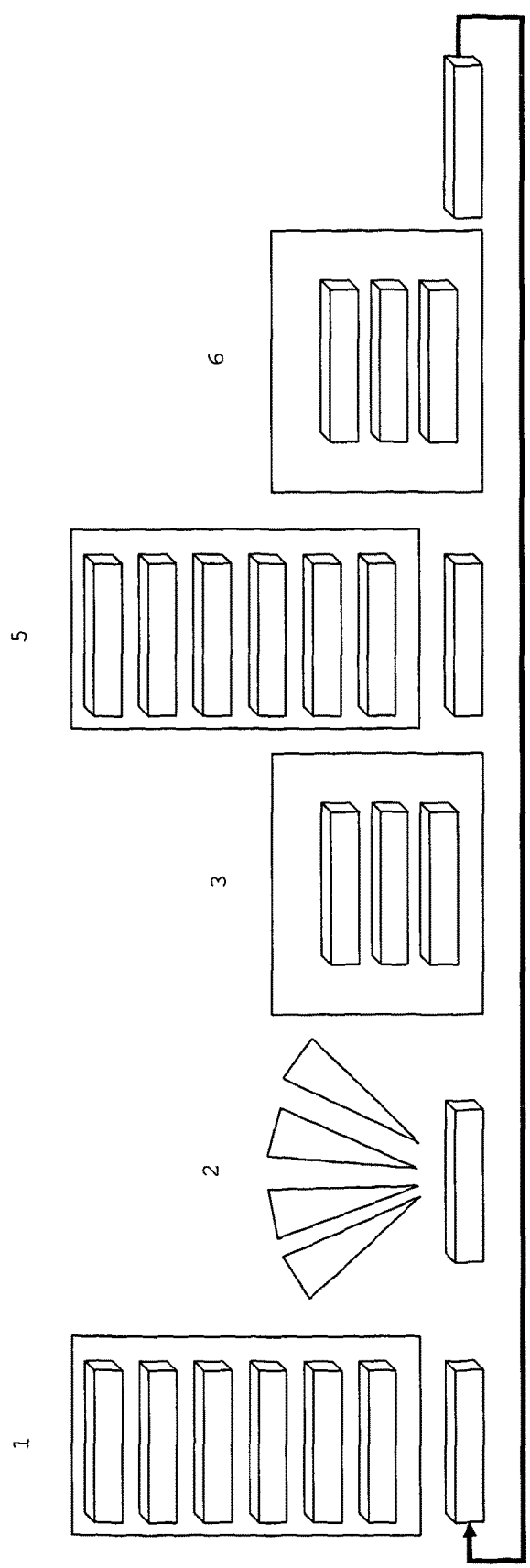

FIG. 8 shows an apparatus according to an embodiment of the invention which comprises a linear set of processing stations. Station 1 is a plate stack station to present new multiwell plates to the system. Station 2 is a dispensing station which adds liquid reagents to wells in the plates. For example, the station may dispense collagen solution, buffer, nutrients, and cells to the wells, or a cell suspension, for example to seed the surface of a construct in the well. Station 3 is an incubation station which maintains the wells in the plate at a raised temperature (e.g. 37° C.) to set the collagen solution in the wells or to incubate cells in or on the constructs. Station 4 is a plunger loading station where fresh plungers are loading onto the plunger holders of an apparatus for compression. Station 5 is a compression station where the plungers loaded at station 4 are used to compress the gel which was set in the wells of the plates at station 3. Station 6 is a plunger removal station where used plungers are unloaded.

Figure 9:
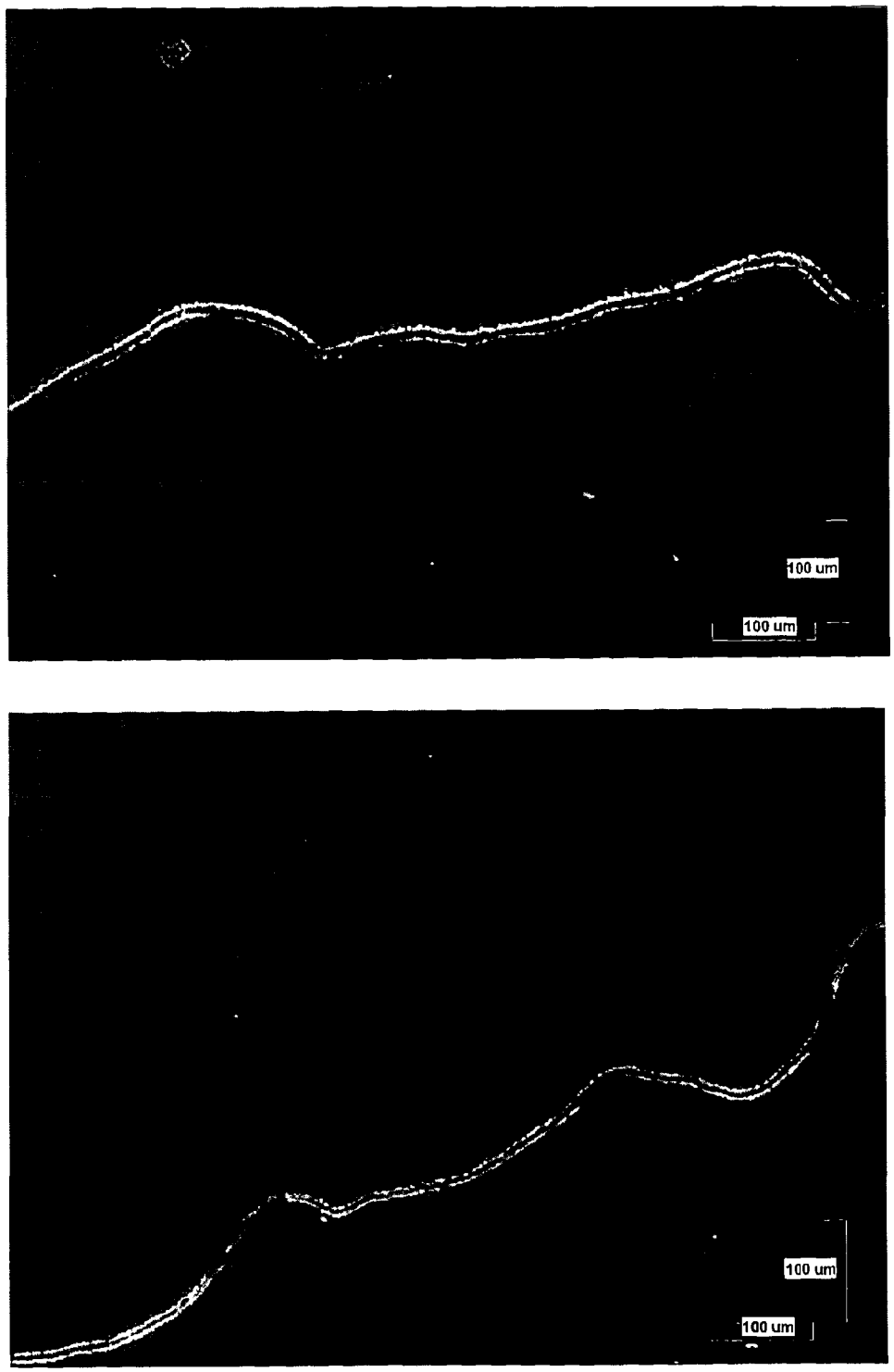

FIG. 9 shows the results of haematoxylin and eosin (H&F) histological staining of a biomimetic construct (cross-section) produced as described herein with the apparatus shown in figures and 7. Cross sections of biomimetic constructs produced in two separate wells simultaneously by the apparatus are shown.

Figure 10:
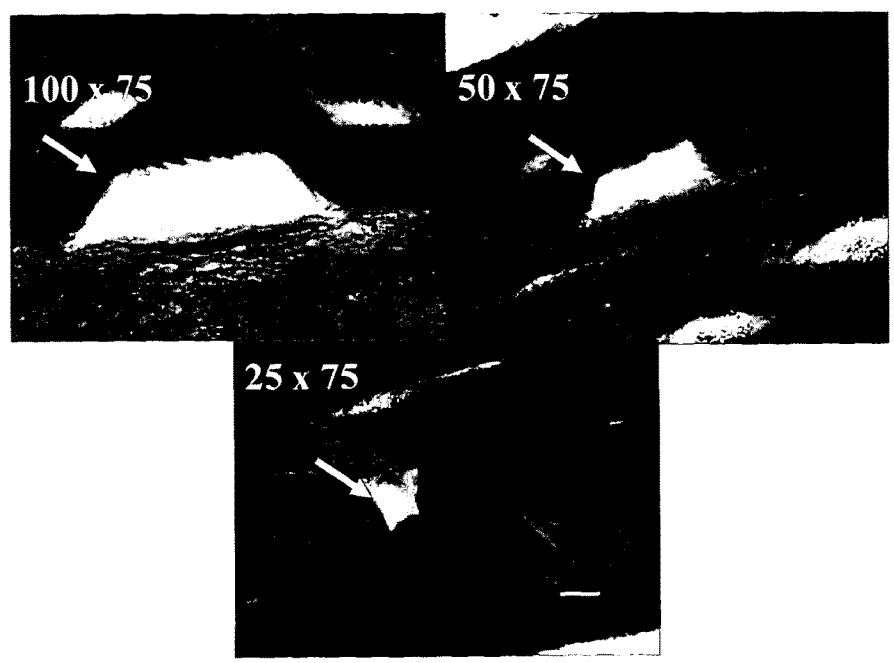

FIG. 10 shows representative images of roofed microchannels in double-layered PC collagen constructs embossed using projections of different dimensions. Scale bar 20 µm. Arrows show the opening of the channels.

A method of producing a biomimetic construct according to an embodiment of the invention is shown in FIG. 1. The production of a construct in a single well is described, but constructs ay be produced in an array of wells simultaneously in the same way.

Figure 1A:
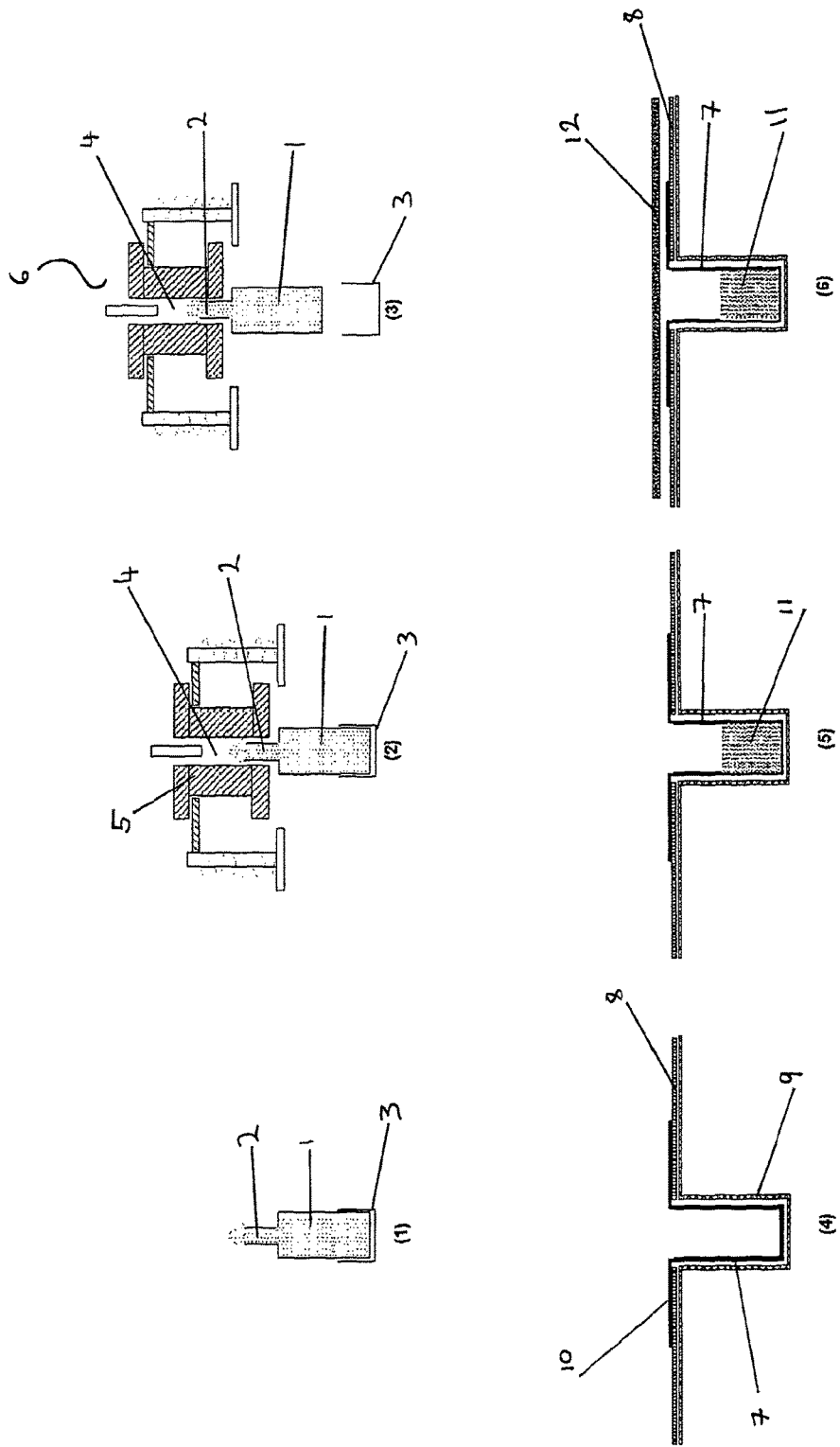
FIG. 1 shows a schematic of an example of a method of the invention.

A porous plunger 1 with an impermeable connector 2 on top is provided in a tray 3 that can hold 24 plungers (FIG. 1a #1).

The tray is placed onto the collagen compression apparatus (not shown) and the aperture 4 of a plunger holder 5 is forced into contact with the plunger connector 2 (FIG. 1a #2).

The plunger head 6, which contains the entire mechanism holding the plunger, is then lifted, lifting the plunger 1 held in the plunger holder 5 from the tray 3 (FIG. 1a #3). The tray 3 is then discarded.

A well (which may also be referred to as an insert) is placed into position on a mounting plate 8. The bottom of the well 7 may be porous. The well has flanges 10 that rest on top of the mounting plate 8. The mounting plate is placed onto a support 9. The support 9 may be a multiwell plate. The support 9 is shown in FIG. 1a #4 with cross-hatching; the mounting plate 8 has vertical hatching; the well 7 has a solid outline.

The well 7 is then filled with collagen solution 11 FIG. 1a #5. Optionally, the collagen solution 11 may be seeded with cells before or after introduction to the well 7.

The mounting plate 8 containing the well 7 is then covered with a lid 12 and the collagen solution 11 is incubated to form a gel (FIG. 1a #6) The lid 12 is shown in FIG. 1a #6 as a densely dotted line.

Figure 1B:
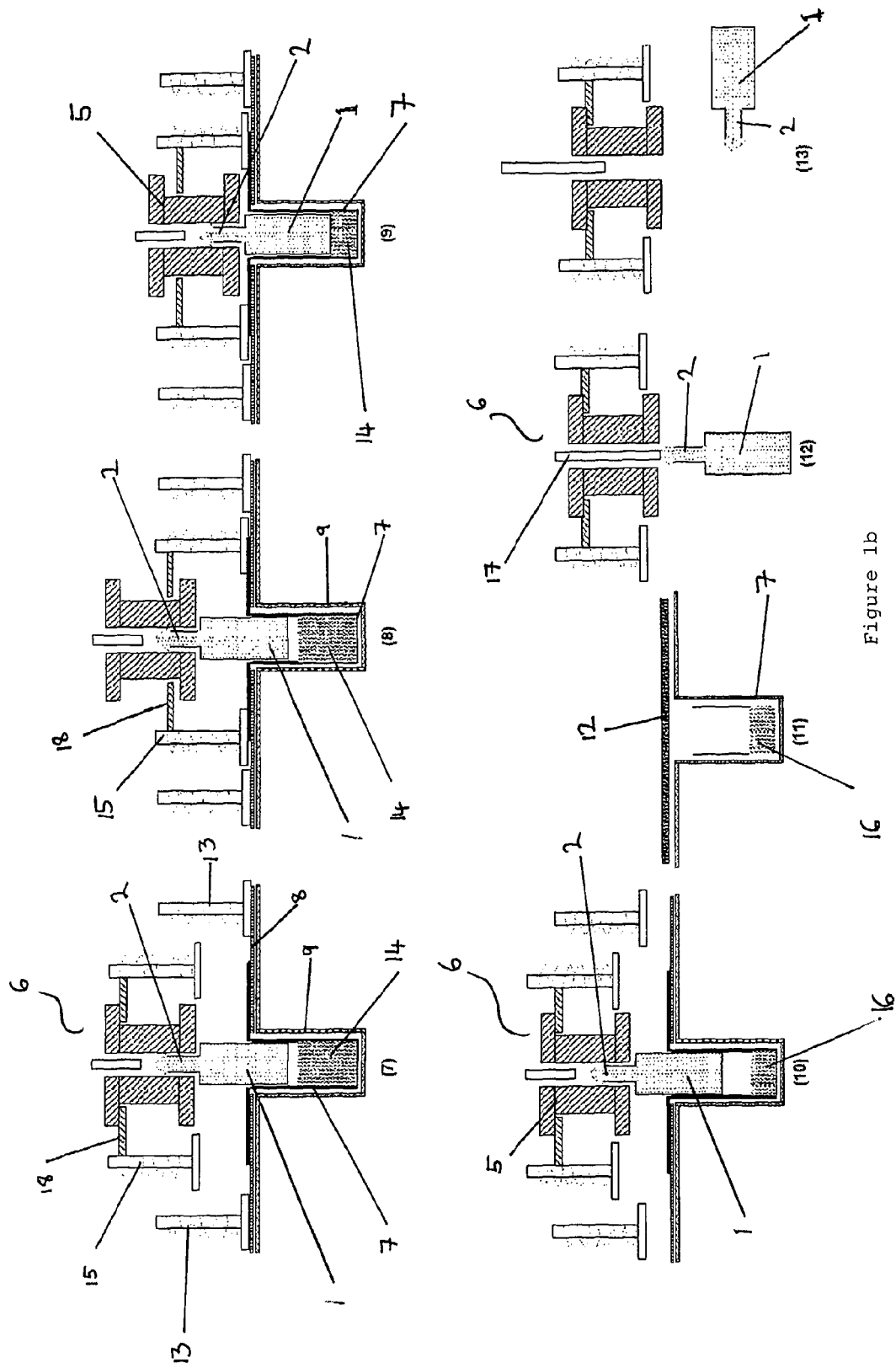

The lid 12 is then removed and the plunger head 6 is moved over the mounting plate 8 (FIG. 1b #7). The head 6 is lowered so that the mounting plate 8 is secured into position with the outer resilient guide 13. The plunger 1 is held in the plunger holder 5 above the collagen gel 14 in the well 7.

The well 7 is then secured in position with inner resilient guides 15 that force the well to the bottom of the support 9, thereby preventing expulsion of liquid from the bottom of the well 7, when a well 7 with a permeable bottom is employed. The plunger 1 is made to move toward the bottom of the well 7 through the release of the plunger holder 5, which grips the plunger 1 in its aperture 4. The plunger holder 5 is movably held within the plunger head 6 by the stop 18, which limits the movement of the plunger holder 5 (FIG. 1b #7) until it is released (FIG. 1b #8)

The downward movement of he plunger holder 5 moves he plunger towards the bottom of its well 7, compressing the collagen gel 14 in the well 7 and absorbing liquid expelled from it FIG. 1b #9.

After compression, the plunger head 6 is raised, lifting the plunger 1 held in the plunger holder 5 out of the well 7. The mounting plate 8 is freed, and the head 6 is moved away from the well 7 containing compressed collagen 16 (FIG. 1b #10).

The lid 12 then placed back over the well 7 to keep the compressed collagen 16 clean and facilitate incubation.

The plunger 1 is then released from the plunger head 6 by probe 17 which through the aperture 4 of the plunger holder 5 and dislodges the connector 2 of the plunger 1.

The plunger 1, which contains the liquid expelled from the gel 14 during compression, is then discarded.

Figure 2B:
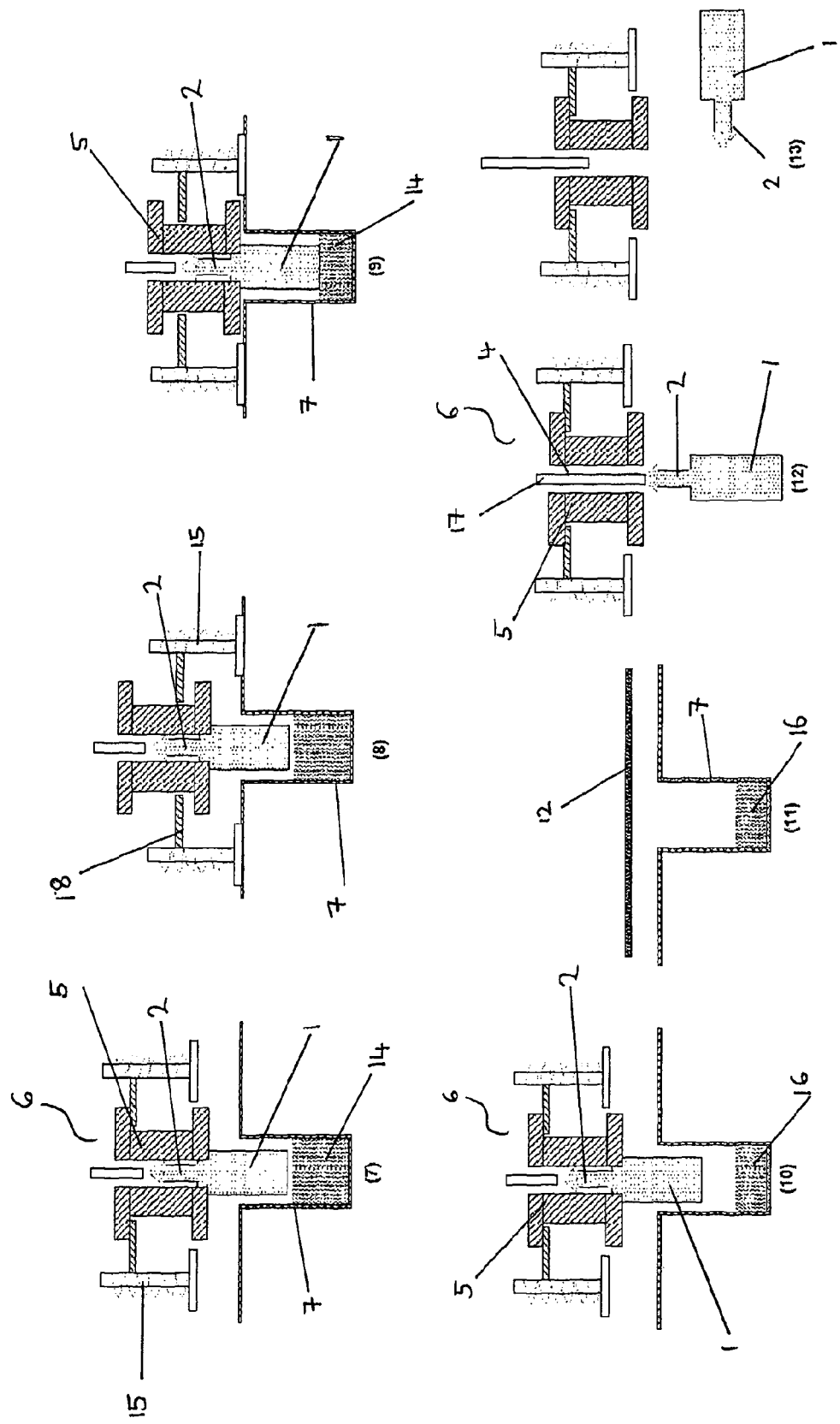
FIG. 2 shows a schematic of another example of a method of the invention.

Another embodiment of a method of producing a biomimetic construct is shown in FIGS. 2a and 2b. The method is similar to that shown in FIGS. 1a and 1b except the wells 7 are integral to the support 9 (FIG. 2a #4). Unlike FIGS. 1a and 1b, separate wells and mounting plates are not required. A guide plate may optionally be used to facilitate proper positioning of the plungers into their respective wells. In this embodiment, the plunger 1 moves down directly into the well 7 in the support 9 and may therefore display a slightly larger diameter than that used with a separate insert well.

Collagen solution 11 is dispensed directly into the well 7 in the support 9 (FIG. 2a #5)

A lid 12 is placed directly over the support 9 to incubate the collagen solution 11 in the well 7 and cause it to set to produce a collagen gel (FIG. 2*a* #6).

The lid 12 is then removed and the plunger head 6 is moved over the support 9 (FIG. 2*b* #7). The plunger 1 is held in the plunger head 5 above the collagen gel 14 in the well 7.

The well 7 is then secured in position with the inner resilient guides 15 which are connected to the plunger stop 18. The contact between the inner resilient guides 15 and the support 9 disengages the plunger holder 5 from the plunger stop 18 and causes the plunger 1 to move towards the bottom of the well 7. The plunger holder 5 is movably held within the plunger head 6 by the stop 18, which defines the extent of the upward and downward movement of the plunger holder 5 (FIG. 2*b* #8).

The downward movement of the plunger holder 5 moves the plunger 1 towards the bottom of the well 7, compressing the collagen gel 14 in the well 7 and absorbing liquid expelled from it FIG. 2*b* #9.

After compression, the plunger head 6 is raised, lifting the plunger 1 held in the plunger holder 5 out of the well 7. The support 9 is freed, and the head 6 is moved away from the well 7 containing compressed collagen 16 (FIG. 2*b* #10).

The well 7 is then covered by the lid 12 to keep the compressed collagen 16 clean and facilitate incubation (FIG. 2*b* #11).

The plunger 1 is then released from the plunger head 6 by probe 17 which through the aperture 4 of the plunger holder 5 and dislodges the connector 2 of the plunger 1 (FIG. 2*b* #12).

The plunger 1, which contains the liquid previously expelled from the gel during compression, is then discarded (FIG. 2*b* #13).

Figure 3:
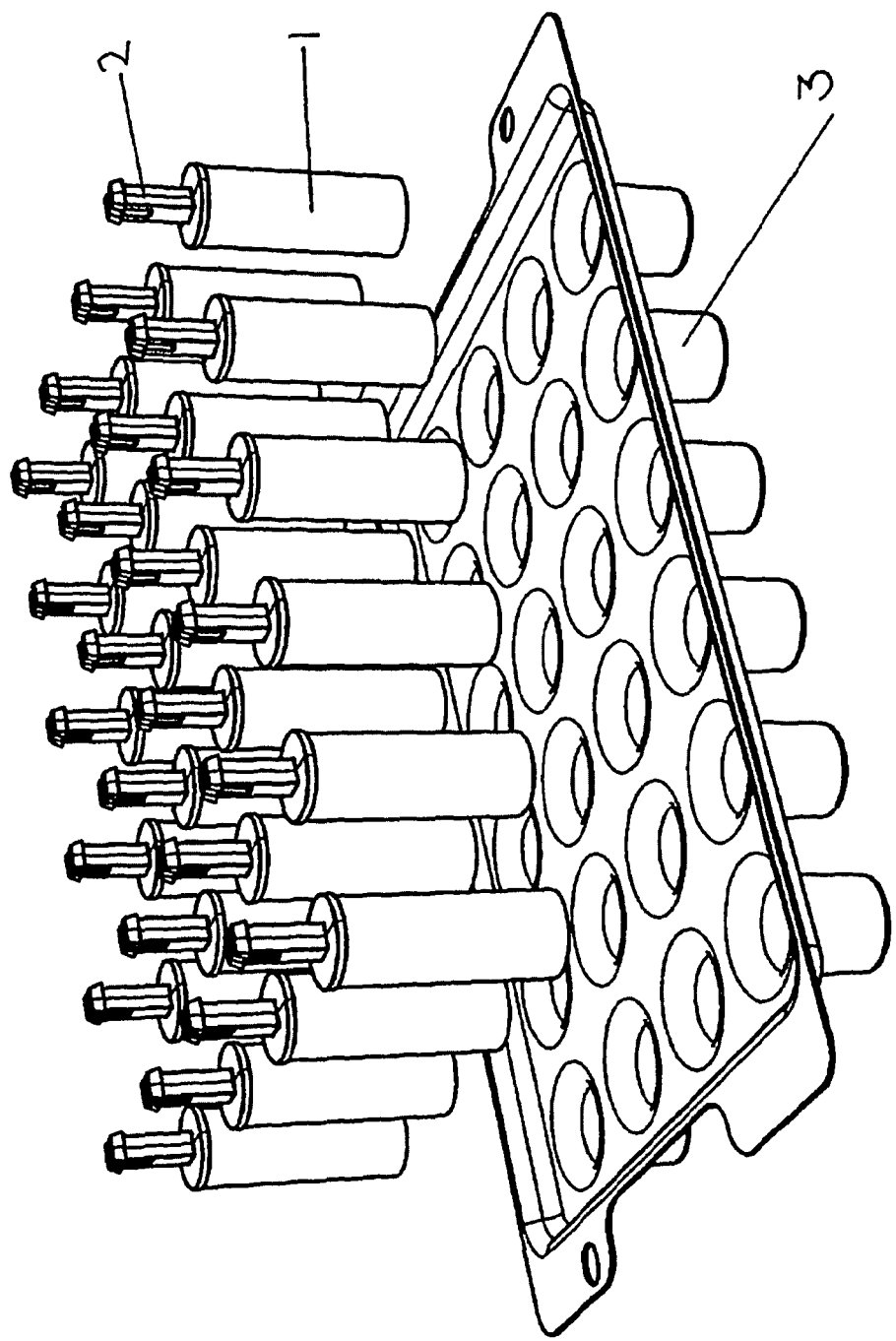
FIG. 3 shows an array of plungers which may be used in kits of the invention in a disposable tray.
Figure 4:
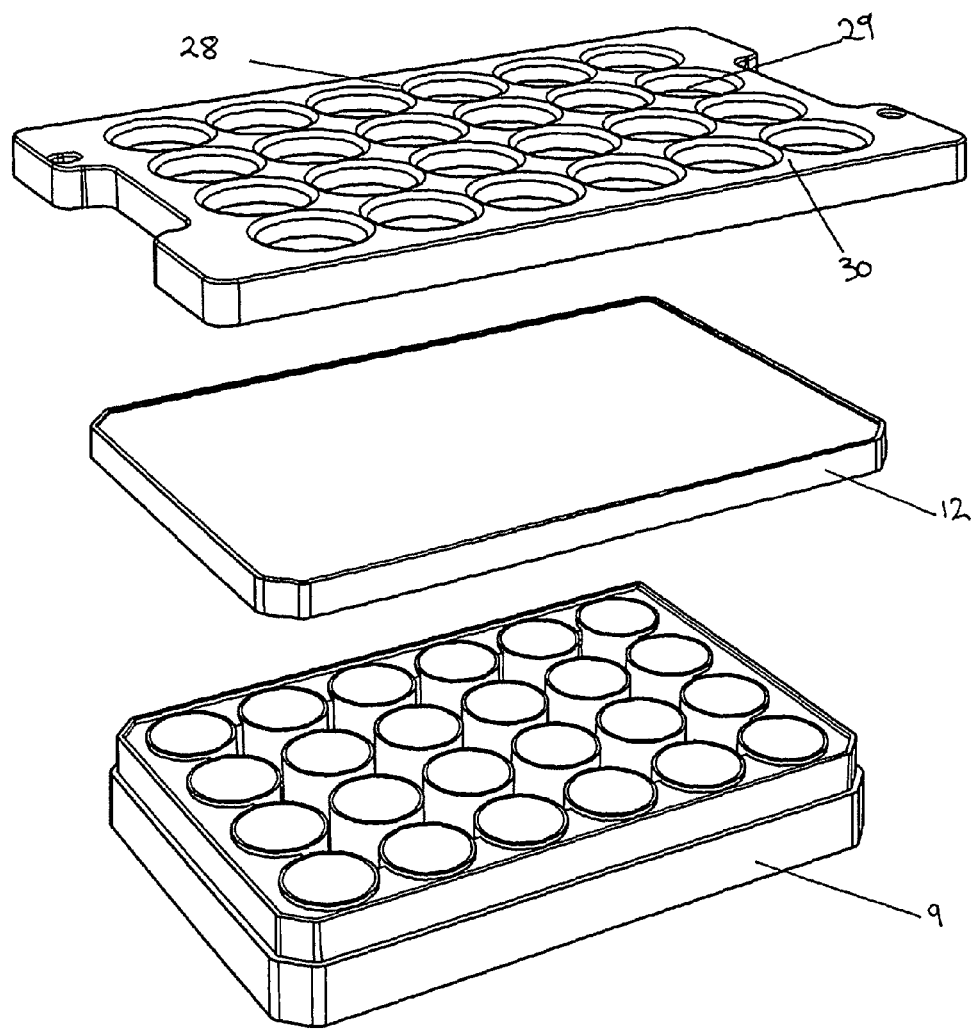
FIG. 4 shows a support containing integral wells which may be used in kits of the invention, along with a lid for covering the wells of the support and a guide plate for guiding plungers to the wells.

An array of plungers 1 for compressing gels in an array of wells is shown in FIG. 3. The plungers 1 are mounted with their connectors 2 uppermost in a disposable presentation tray 3 which positions the plungers 1 for loading onto the plunger holders of a collagen compression apparatus.

An impermeable support 9 is shown in FIG. 2. An array of wells 7 is integral to the support A lid 12 is used to cover the wells 7 during incubations and storage. A guide plate 28 may be used to cover the wells 7 during compression. The guide plate 28 contains an array of apertures 29 which correspond to the wells 7 in the support 9. The apertures 29 are tapered i.e. the internal diameter of the apertures at the upper surface 30 of the guide plate is greater than the internal diameter at the lower surface of the guide plate. At the lower surface of the guide plate, the apertures 29 have the same internal diameter as the wells 7 in the support 9. The guide plate 28 guides plungers as they move downwards into the wells 7 of the support 9.

Figure 5:
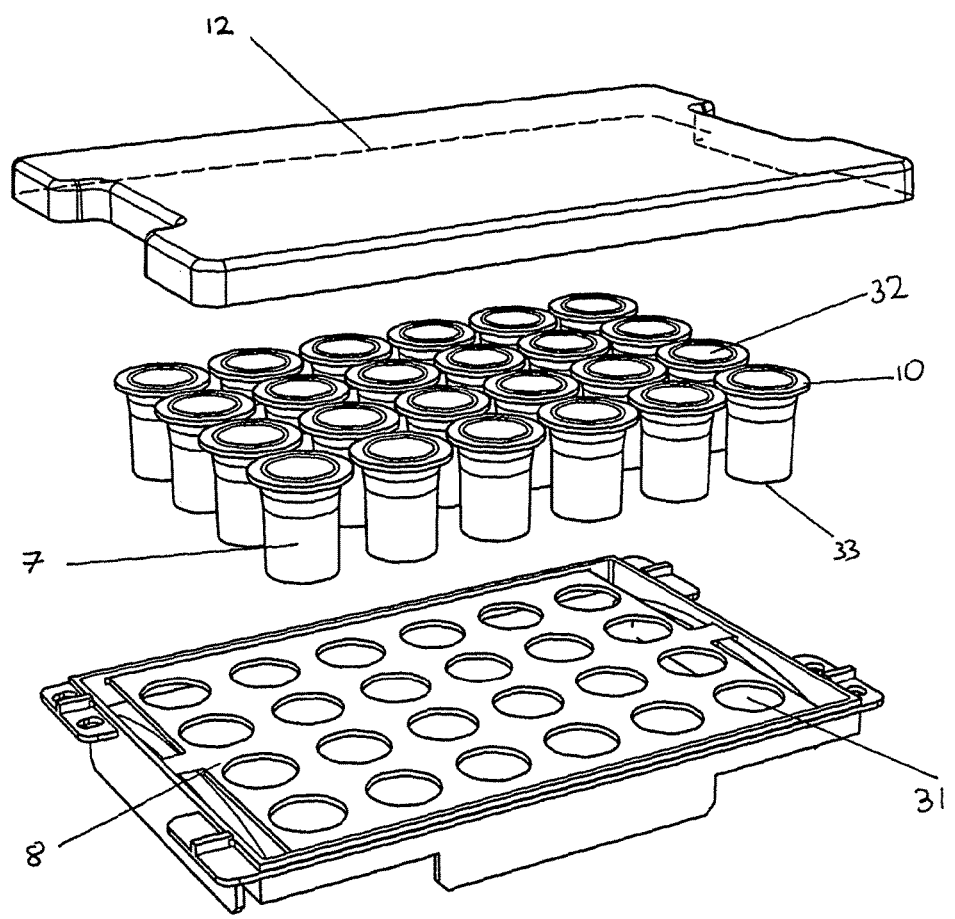
FIG. 5 shows individual wells inserted into a mounting plate with a lid, which may be used in kits of the invention.

An array of individual wells 7 is shown in FIG. 5. The wells 7 are tapered so that the internal diameter at the opening 32 is greater than the internal diameter at the bottom of the well 33. The wells 7 are mounted in apertures 31 in the mounting plate 8. The flanges 10 of the wells 7 rest on the mounting plate 8 and prevent the wells 7 from falling through the apertures 31. A lid 12 is used to cover the wells 7 in the mounting plate during incubation and storage.

The operation of an apparatus for simultaneously producing biomimetic constructs in an array of wells is shown in FIG. 6.

Figure 6A:
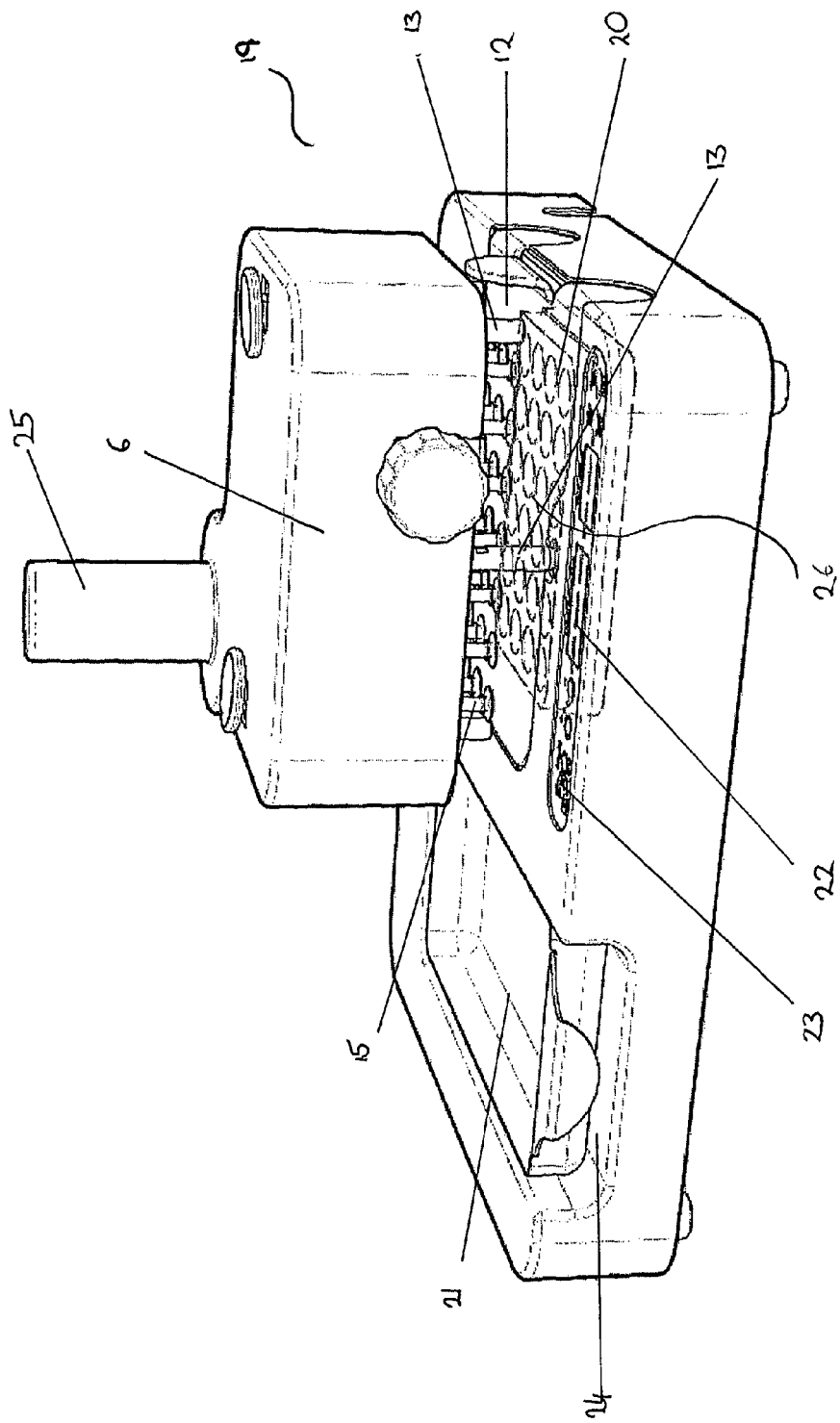
FIGS. 6a to 6g show a schematic of an apparatus performing a method of the invention.

Initially, the apparatus 19 is in a resting state with the plunger head raised and no consumables, such as plungers or wells, loaded (FIG. 6*a*). The apparatus 19 comprises a plunger head 6 pivotally mounted on a post 25 and movable between a compression station 26 and an unloading station 21. The head 6 contains an array of plunger holders not visible and resilient inner and outer guides 15 and 13.

The compression station 26 comprises a mount 20 for accommodating wells which can be covered by a lid 12. The mount 20 rests on a heated plate not shown to incubate wells accommodated in the mount 20. The apparatus contains a display 22 which indicates the temperature and duration of incubation of wells positioned in the mount and controls 23 to allow these parameters to be adjusted. A removable waste tray 21 s positioned in an unloading station 21.

Figure 6B:
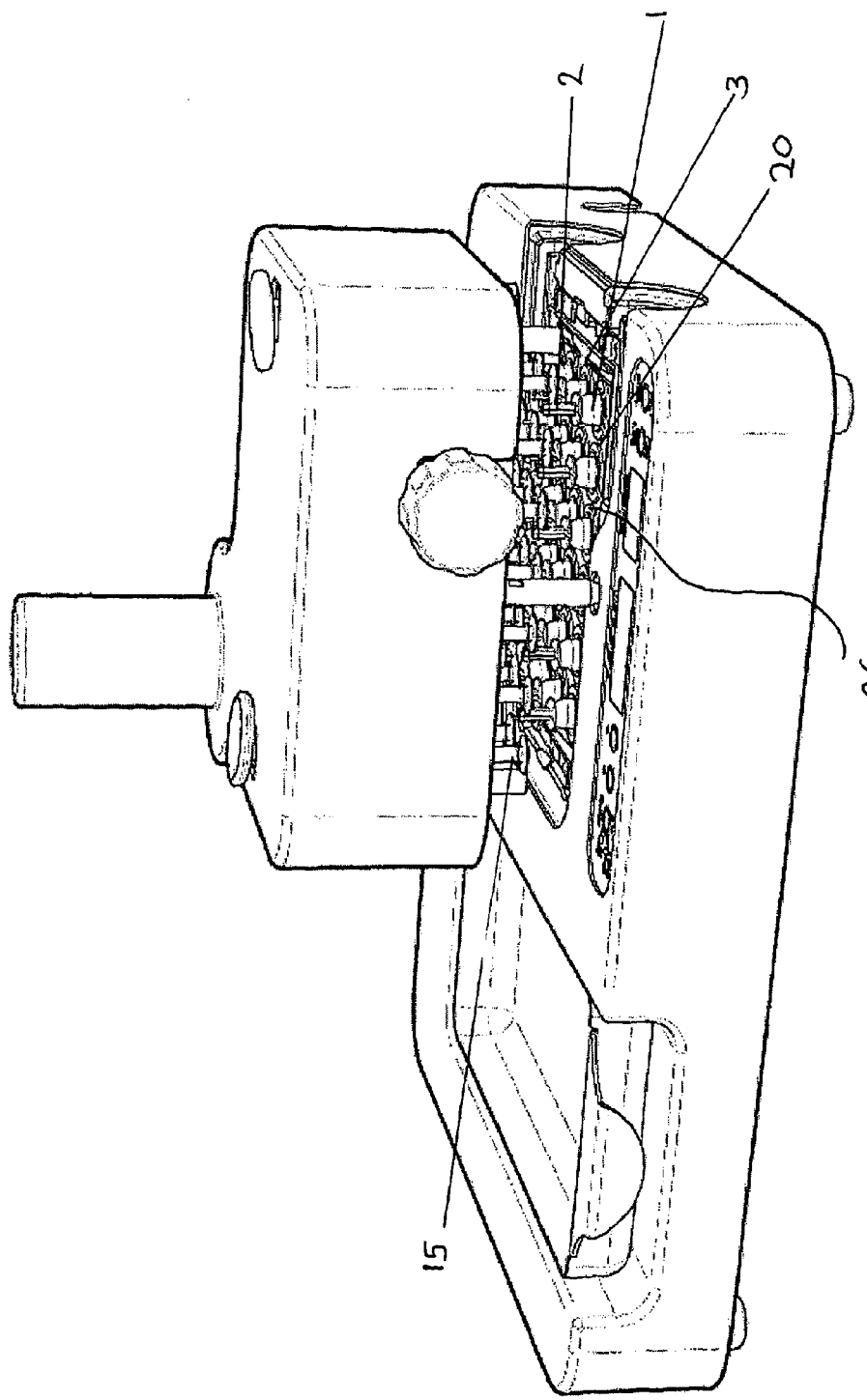

In a first stage, the plunger holders 5 within the plunger head 6 are loaded with plungers 1. A tray 3 containing an array of plungers 1 is positioned on the mount 20 and the connectors 2 of the plungers 1 are introduced to the apertures of the array of plunger holders not visible mounted in the plunger head 6. The engagement of the connector 2 with the aperture holds each plunger 1 in its corresponding plunger holder 5, so that the array of plungers 1 can be lifted from the tray 3 by the plunger head 6 (FIG. 6*b*). This stage is also shown schematically in steps 1 and 2 of FIGS. 1 and 2.

Figure 6C:
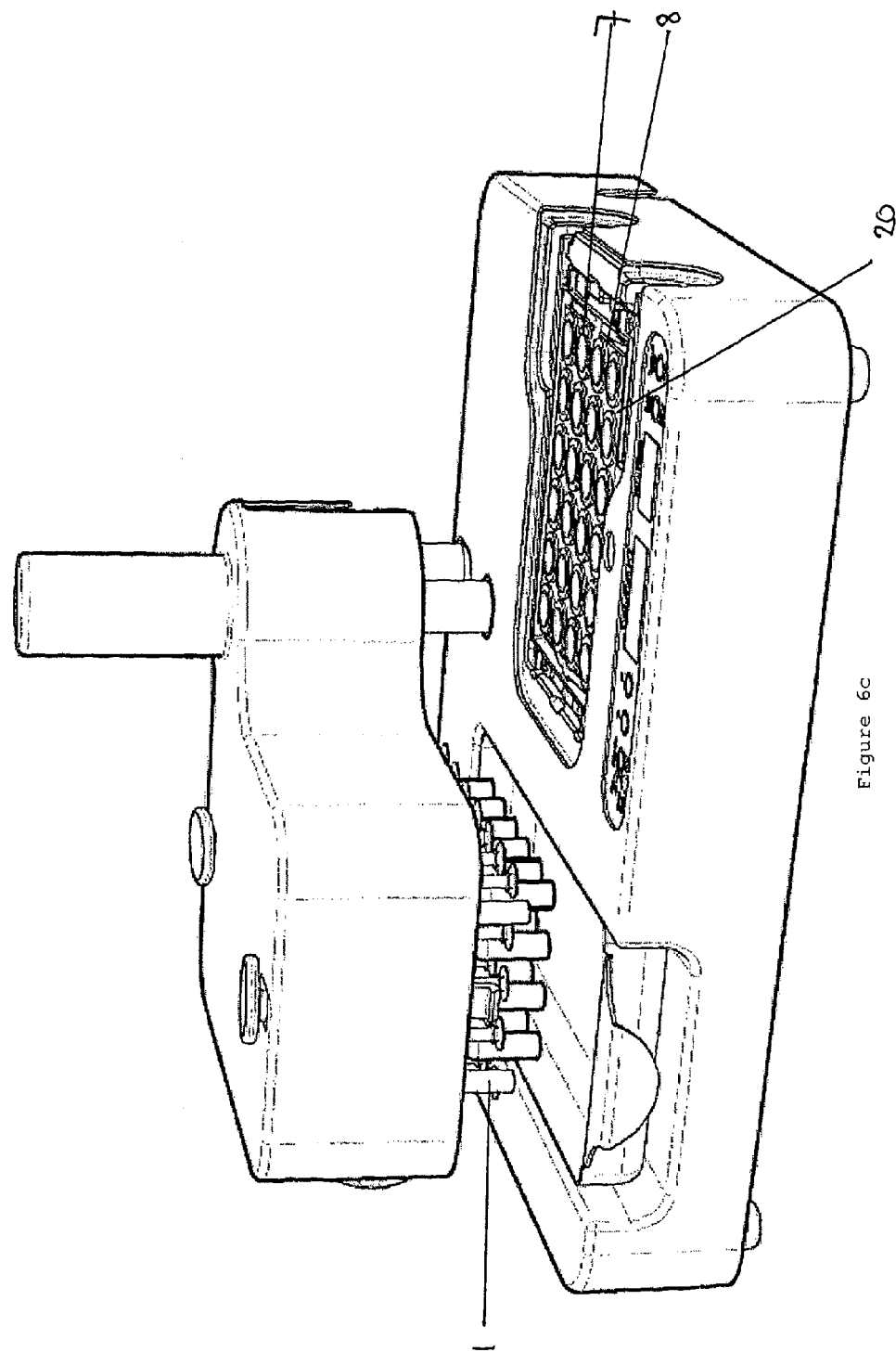

The plunger head 6 loaded with the array of plungers 1 is then moved aside by pivoting it around the post 25 to be positioned over the waste tray 21. The wells 7 are positioned in a mounting plate 8 on the support 9 in a 24 well array and then introduced to the mount 20. With the plunger head 6 positioned over the waste tray 21, the wells 7 are accessible for the introduction of collagen solution; suspensions of cells; and/or other reagents (FIG. 6*c*). This stage is also shown schematically in steps 3, 4 and 5 of FIGS. 1 and 2.

Figure 6D:
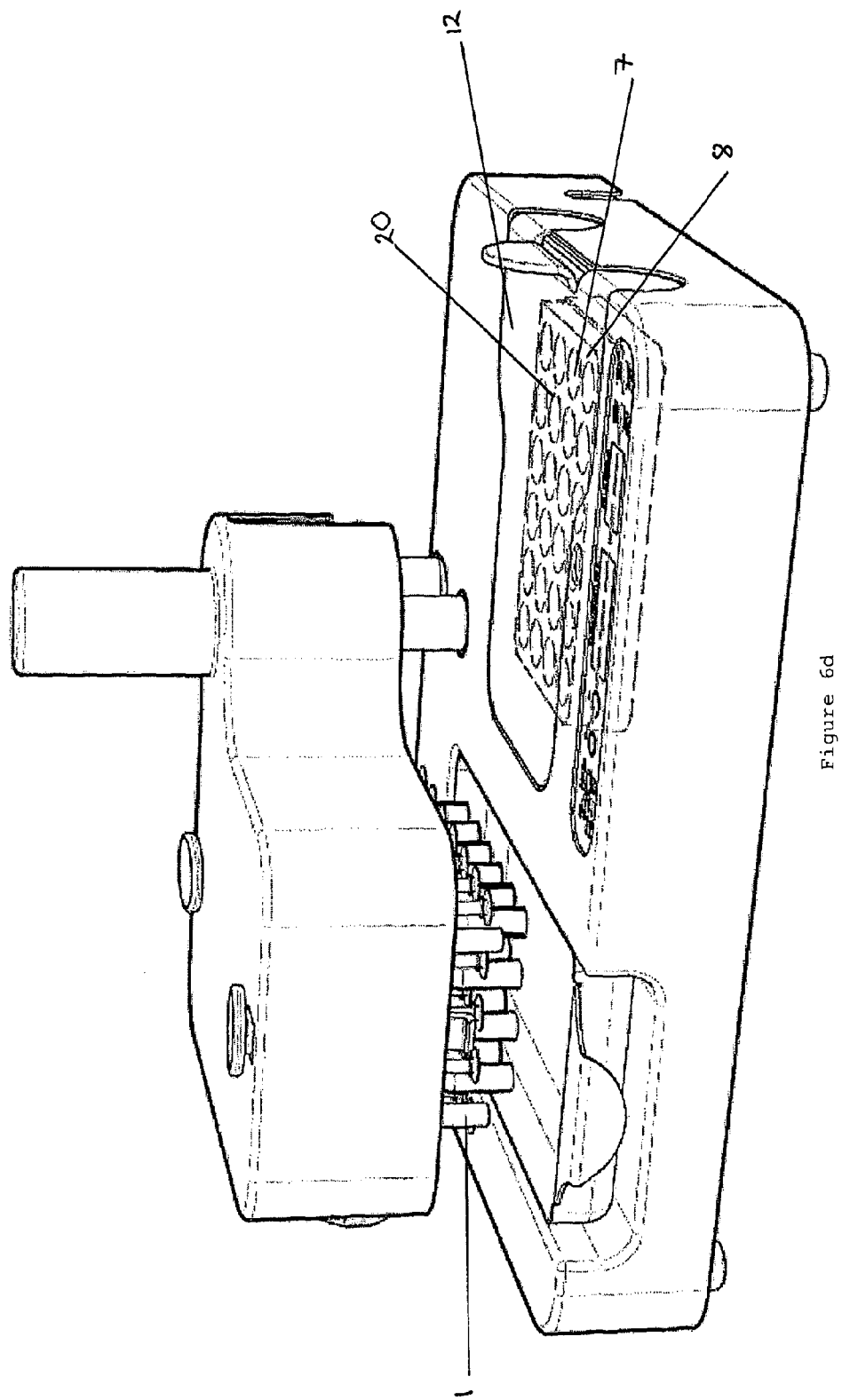

Whilst the loaded plunger head 6 is positioned over the waste tray 21, the wells 7 in the mounting tray 8 are filled with collagen solution (not visible), optionally seeded with cells, and covered with a lid 12. The wells are then heated in the covered mount 20 by the heater (not shown) and incubated at 37° C. to cause the collagen solution to set into a gel (FIG. 6*d*). This stage is also shown schematically in step 6 of FIGS. 1 and 2.

Figure 6E:
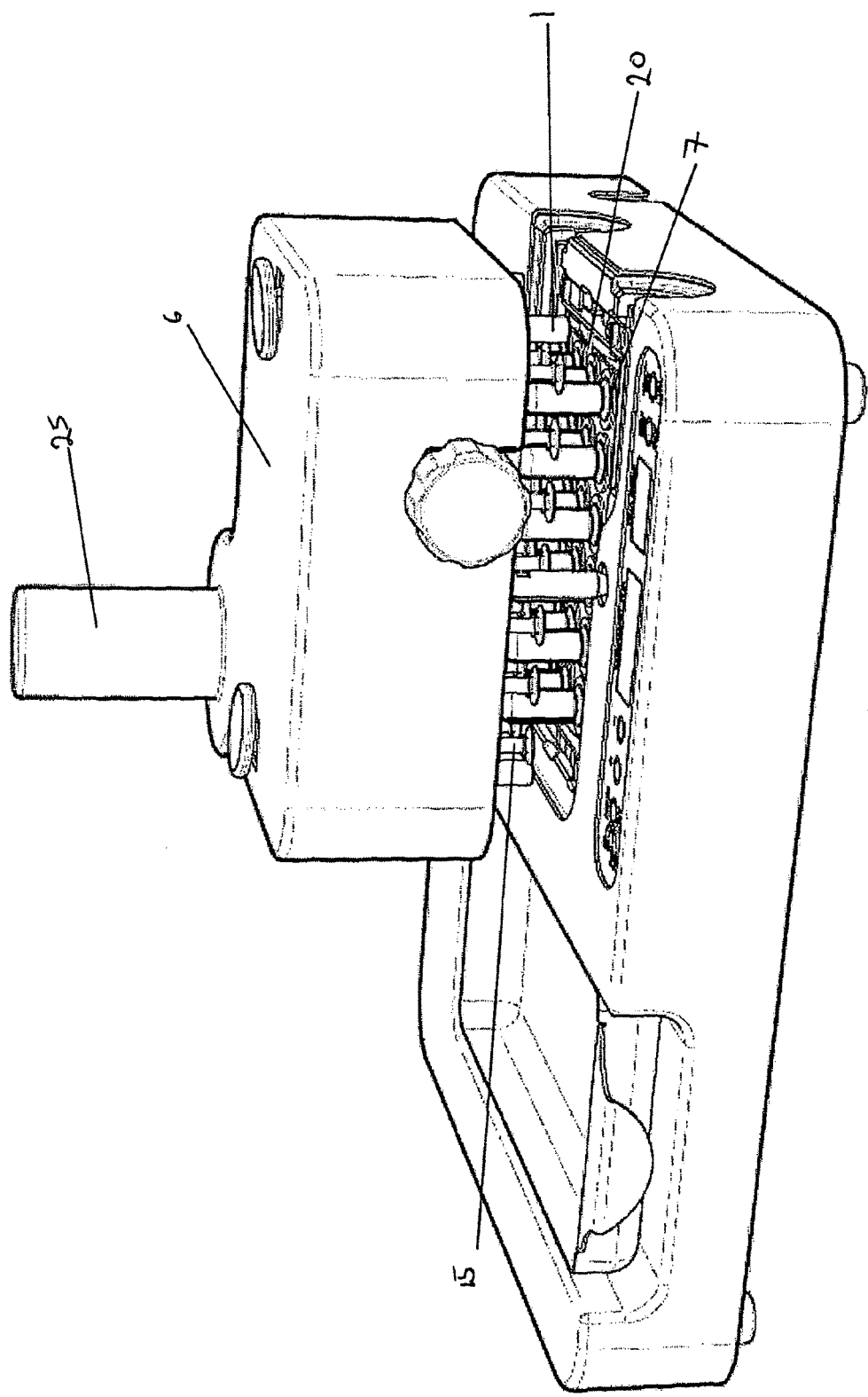

The lid (not shown) is then removed from the mount 20 and the plunger head 6 is pivoted around the post 25 into a position over the wells 7, so that the plungers 1 attached to the plunger holders (not visible) are ready to insert into the wells 7 of the plate (FIG. 6*e*). This stage is also shown schematically in step 7 of FIGS. 1 and 2.

Figure 6F:
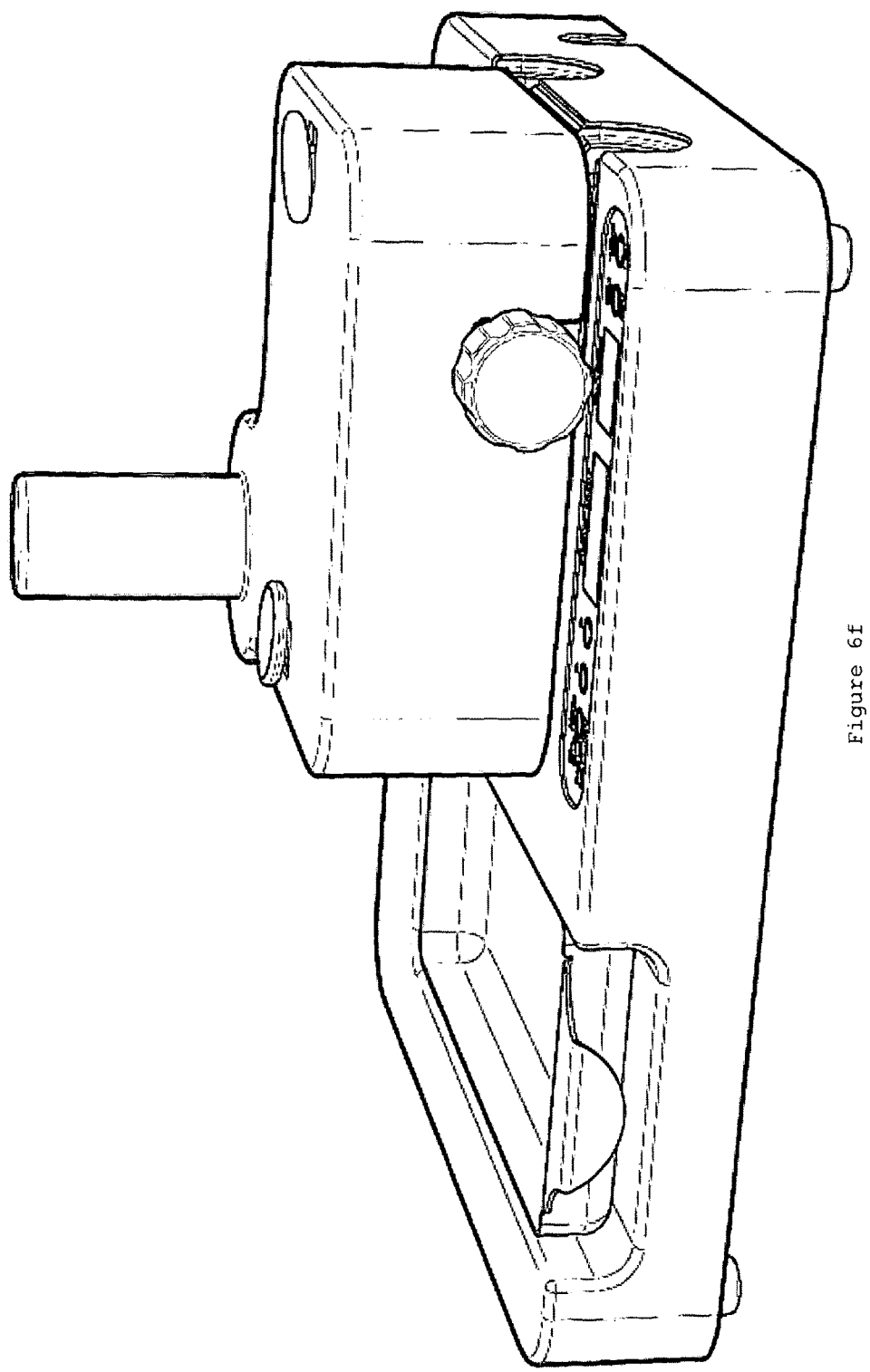

The plunger head 6 is then latched down so that the plungers 1, which are weighted by the plunger heads (not visible), rest on the gel (not visible) in each well 7. The plungers 1 compress the collagen gel not visible and absorb the liquid expelled from the gel by the compression (FIG. 6*f*). This stage is also shown schematically in steps 8 and 9 of FIGS. 1 and 2.

The plunger head 6 is then lifted, so that the plungers 1, which now contain expelled liquid from the compressed gel in the wells 7, are removed from the wells 7 in the mount 20. This stage is also shown schematically in step 10 of FIGS. 1 and 2.

Figure 6G:
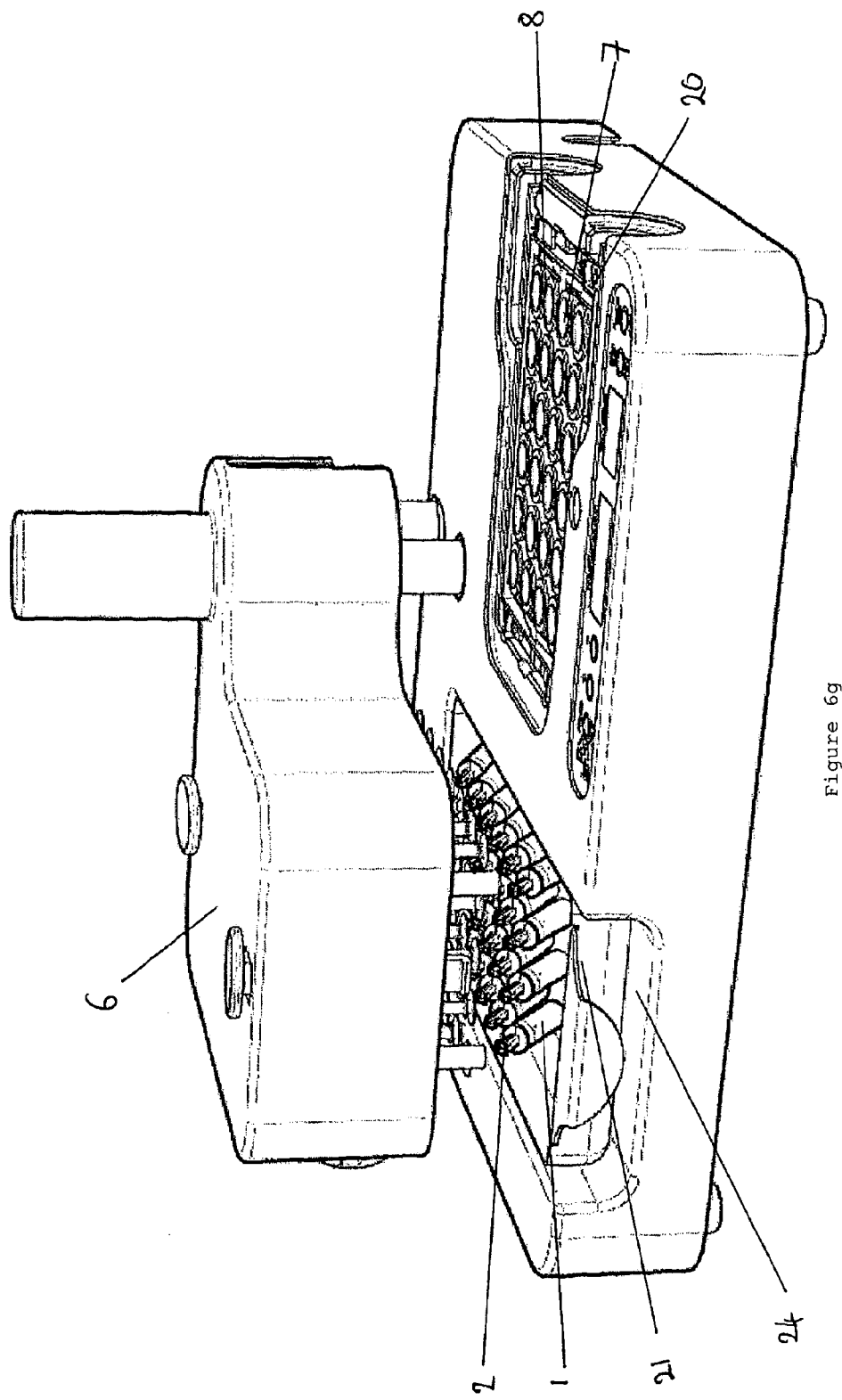

The plunger head 6 containing the wet plungers 1 is then pivoted around the post 25 and positioned over the waste tray 21 in the unloading station 24. The wet plungers 1 are then ejected into the waste tray 21. The wells 7 of compressed collagen remain in position in the mounting plate 8 in the mount 20, without being covered by the lid (FIG. 6*g*). This corresponds to steps 11 to 13 of FIGS. 1 and 2.

In some embodiments, the waste tray 21 may be removed and the plunge holders 1 in the plunger head 6 may be loaded with fresh plungers 1. Additional collagen solution, optionally seeded with cells, may be added to the compressed collagen in the wells 7. The steps shown in FIGS. 6c to 6g may then be repeated to produce a multilayered collagen construct in the wells 7.

The method may be repeated until the constructs in the wells possess the desired number of layers of compressed collagen.

Figure 7:
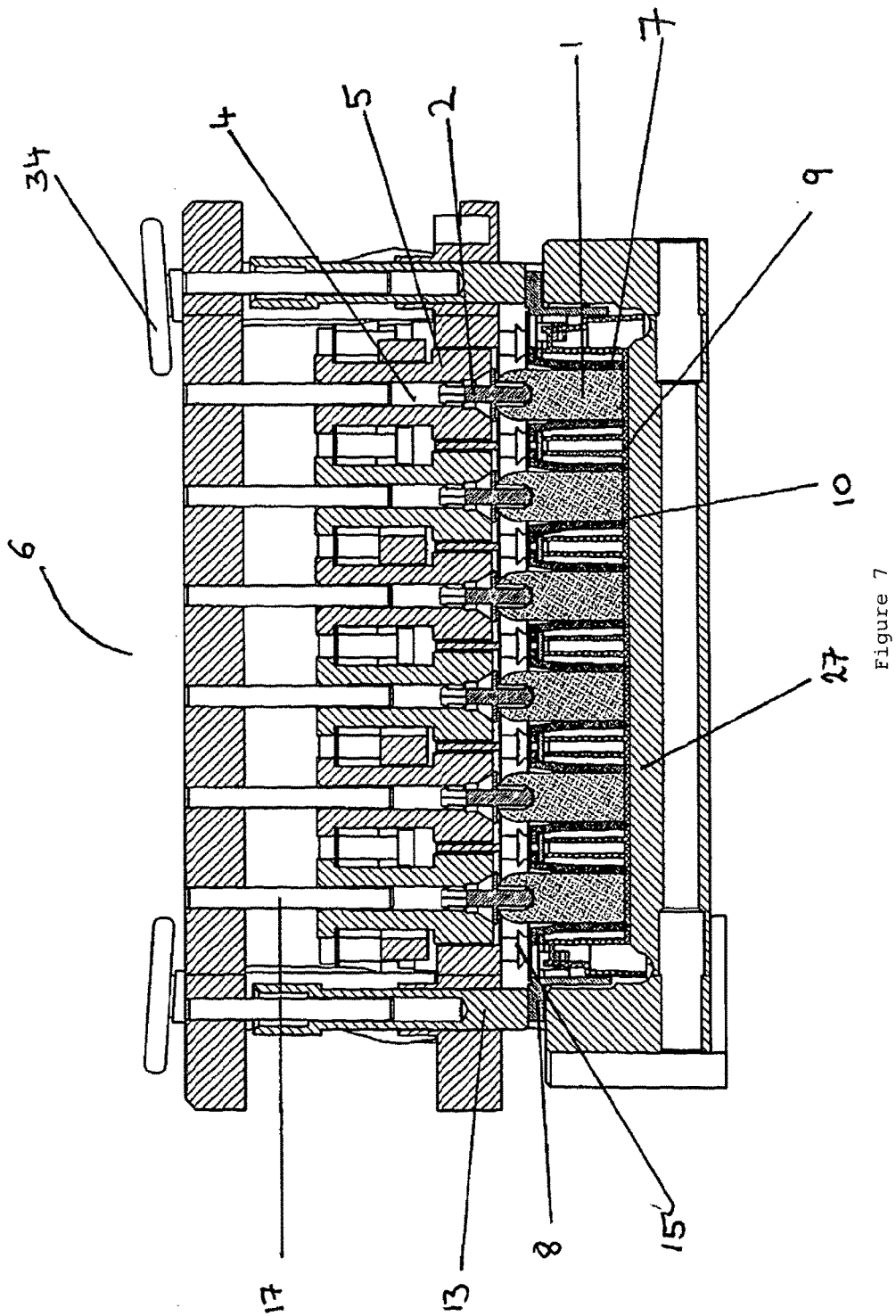
FIG. 7 shows a cross-section of the plunger head of an apparatus according to an embodiment of the invention.

A cross section of the plunger head 6 of the apparatus 19 for producing biomimetic constructs of FIG. 6 is shown in FIG. 7. An array of plungers 1 is held in an array of plunger holders 5 by the frictional engagement of connectors 2 with apertures 4 within the plunger holders 5. The plungers 1 are shown touching the bottoms of an array of wells 7 which are accommodated in a mounting plate 8 on a support 9 positioned on a heating base plate 27. The wells 7 do not contain collagen.

The plunger head is aligned on the mount and the mounting plate 8 is secured by the outer guides 13. A latch 34 secures the head an position. The wells 7 have flanges 10 at their openings which rest on the mounting plate 8. During compression, inner guides 15 secure the wells 7 on the mounting plate 8 and drive the bottom of the wells 7 against the support 9. The individual plunger holders 5 are released from the head 6 and exert a gravitational force on the plungers 1 in the wells 7.

A probe 17 is engaged in the aperture 4 of each plunger holder 5 and can be moved downwards to dislodge the connector 2 and eject the plunger 1 from the plunger holder 5 after use.

FIG. 8 shows a multistation apparatus of the invention. Plates containing wells may move through one or more of the stations several times. For example, after one pass through each station, a plate may pass for a second time through the dispensing station for an intermediate layer of cells, followed by the dispensing station again for a new collagen layer, followed by incubation, plunger addition, compression, and plunger removal.

Cross sections of biomimetic constructs produced with the apparatus shown in FIGS. 6 and 7 were stained with haematoxylin and eosin H&E). The results are shown in FIG. 9. A dense collagenous structure was observed with human dermal fibroblast cells (initial density 100,000 cells/ml) dispersed throughout the structure, akin to the anatomy of the dermis layer of skin. This demonstrates that the constructs produced by the apparatus described herein are highly biomimetic.

Two-part micro-channels were created by template micromoulding using unidirectional fluid flow in a multi-well format. In first stage, grooves were embossed in the surface of one layer. In the next stage, a layer of fresh collagen solution was set over the top of these grooves and compressed onto the first to act as a micro-channel 'roof'. This technique (producing 'roofed μ-channels') allowed for simple and rapid fabrication of controlled thickness constructs with pre-formed channels. The dimensions of the channels were found to be a predictable proportion of stamp or template used for moulding. Under the conditions used, the proportion was between 20% and 50% and for 75 μm and 125 μm deep stamps, channels were typically formed as 25 μm and 50 to 100 μm wide and up to 30 μm deep (FIG. 10). The compressed collagen matrix was made with viable cells in place which grew and remodelled the matrix for some weeks, though the channels remained. Channel walls were made from compacted, orientated collagen fibrils which accumulated around the mould during compression, providing durability in culture. Detailed study of the relationship between template dimensions and the channels ultimately produced has shown that moulding fidelity is sensitive to stamp shape and collagen density. These results demonstrate that plastic compression with moulding and multi-layering can be used to make highly predictable μ-channelled, living 3D constructs with good perfusion.

The invention claimed is:

1. A method of producing a biomimetic construct comprising:
    (i) introducing a gel solution to a well having an opening,
    (ii) incubating the gel solution to form a gel,
    (iii) introducing a porous plunger to the well,
    (iv) compressing the gel with the porous plunger such that liquid is expelled from the gel through a surface of the gel that is contacted by the porous plunger, the liquid, prevented from being expelled through the well bottom, entering the porous plunger and the volume of the gel being reduced, thereby producing the biomimetic construct, wherein a volume of the liquid expelled from the gel into the plunger per unit of surface area of the plunger that contacts the gel is about 2 mm to about 14 mm, and
    (v) removing the porous plunger containing expelled liquid to leave said biomimetic construct in the well.

2. A method according to claim 1 wherein the gel solution is seeded with cells.

3. A method according to claim 1 further comprising:
    (vi) introducing a further gel solution onto the biomimetic construct in the well,
    (vii) incubating the further gel solution to form a further gel,
    (viii) introducing a porous plunger to the well,
    (ix) compressing the further gel with the porous plunger such that liquid is expelled from the gel into the porous plunger and the volume of the gel is reduced,
    (x) removing the porous plunger to leave a biomimetic construct comprising multiple layers of compressed gel in the well, optionally repeating steps (vi) to (x) one or more times to produce a biomimetic construct comprising multiple layers of compressed gel.

4. A method according to claim 1 wherein the porous plunger comprises one or more projections which emboss recesses, optionally grooves, into the surface of the compressed gel.

5. A method according to claim 1 further comprising seeding the surface of the compressed gel with cells.

6. A method according to claim 1 wherein biomimetic constructs are produced in an array of wells simultaneously.

7. A method according to claim 1 wherein the gel solution is a collagen solution and the gel is a collagen gel.

8. A method of producing a biomimetic construct comprising a roofed channel comprising:
    (i) providing a compressed gel with one or more grooves on the surface thereof,
    (ii) introducing a further gel solution onto the surface of the compressed gel,
    (iii) setting the further gel solution to form a further gel on the surface of the compressed gel, and;
    (iv) compressing the further gel with a porous plunger such that liquid is expelled from the further gel through a surface of the further gel that is contacted by the porous plunger, the liquid, prevented from being expelled through a well bottom, entering the porous plunger and the volume of the further gel being reduced to produce a further compressed gel, wherein a volume of the liquid expelled from the further gel into the plunger per unit of surface area of the plunger that contacts the gel is about 2 mm to about 14 mm, wherein said further compressed gel covering the one or more grooves to produce a biomimetic construct containing a roofed channel.

9. The method of claim 1 wherein compressing the gel with the porous plunger includes expelling at least 95% of the liquid from the gel into the porous plunger.

10. The method of claim 1 wherein a bottom of the well is impermeable or mounted on an impermeable support.

* * * * *